(12) United States Patent
Slayton et al.

(10) Patent No.: US 8,506,486 B2
(45) Date of Patent: *Aug. 13, 2013

(54) ULTRASOUND TREATMENT OF SUB-DERMAL TISSUE FOR COSMETIC EFFECTS

(71) Applicant: Guided Therapy Systems, LLC, Mesa, CA (US)

(72) Inventors: Michael H. Slayton, Tempe, AZ (US); Peter G. Barthe, Phoenix, AZ (US); Inder Raj S. Makin, Mesa, AZ (US); Brian D. O'Connor, Phoenix, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,430

(22) Filed: Nov. 16, 2012

(65) Prior Publication Data
US 2013/0072826 A1    Mar. 21, 2013

Related U.S. Application Data

(63) Continuation of application No. 13/444,336, filed on Apr. 11, 2012, now Pat. No. 8,366,622, which is a continuation of application No. 11/163,151, filed on Oct. 6, 2005, now abandoned.

(60) Provisional application No. 60/616,755, filed on Oct. 6, 2004.

(51) Int. Cl.
*A61B 7/02* (2006.01)

(52) U.S. Cl.
USPC .......................... 600/439; 600/437

(58) Field of Classification Search
USPC .......................... 600/411, 437, 439, 445, 459
See application file for complete search history.

(56) References Cited

U.S. PATENT DOCUMENTS

| 2,427,348 A | 9/1947 | Bond et al. |
| 3,913,386 A | 10/1975 | Saglio |

(Continued)

FOREIGN PATENT DOCUMENTS

| DE | 4029175 | 3/1992 |
| DE | 10140064 A1 | 3/2003 |

(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

(Continued)

*Primary Examiner* — Michael Peffley
*Assistant Examiner* — Ronald Hupczey, Jr.
(74) *Attorney, Agent, or Firm* — Knobbe, Martens, Olson & Bear, LLP

(57) ABSTRACT

A method and system for noninvasive face lifts and tissue tightening are disclosed. The method and treatment system are configured for thermal treatment of Superficial Muscular Aponeurosis System (SMAS) tissue, muscular fascia, or both. In one embodiment, a cosmetic system is configured for treating the SMAS and/or muscular fasica through delivery of ultrasound energy at a depth, distribution, timing, and energy level to achieve the desired therapeutic effect.

20 Claims, 24 Drawing Sheets

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-Huu |
| 4,601,296 A | 7/1986 | Yerushalmi |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose |
| D306,965 S | 4/1990 | Jaworski |
| 4,917,096 A | 4/1990 | Englehart |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry |
| 5,054,310 A | 10/1991 | Flynn |
| 5,054,470 A | 10/1991 | Fry |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,380,280 A | 1/1995 | Peterson |
| 5,391,140 A | 2/1995 | Schaetzle et al. |
| 5,406,503 A | 4/1995 | Williams |
| 5,419,327 A | 5/1995 | Rohwedder |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Lutz |
| 5,840,032 A | 11/1998 | Hatfield et al. |

| | | | | | | |
|---|---|---|---|---|---|---|
| 5,844,140 | A | 12/1998 | Seale | 6,377,855 B1 | 4/2002 | Knowlton |
| 5,853,367 | A | 12/1998 | Chalek et al. | 6,381,497 B1 | 4/2002 | Knowlton |
| 5,869,751 | A | 2/1999 | Bonin | 6,381,498 B1 | 4/2002 | Knowlton |
| 5,871,524 | A | 2/1999 | Knowlton | 6,387,380 B1 | 5/2002 | Knowlton |
| 5,873,902 | A | 2/1999 | Sanghvi | 6,390,982 B1 | 5/2002 | Bova et al. |
| 5,879,303 | A | 3/1999 | Averkiou et al. | 6,405,090 B1 | 6/2002 | Knowlton |
| 5,882,557 | A | 3/1999 | Hayakawa | 6,409,720 B1 | 6/2002 | Hissong |
| 5,891,034 | A | 4/1999 | Bucholz | 6,413,253 B1 | 7/2002 | Koop |
| 5,904,659 | A | 5/1999 | Duarte | 6,413,254 B1 | 7/2002 | Hissong |
| 5,919,219 | A | 7/1999 | Knowlton | 6,419,648 B1 | 7/2002 | Vitek |
| 5,924,989 | A | 7/1999 | Polz | 6,425,865 B1 | 7/2002 | Salcudean |
| 5,928,169 | A | 7/1999 | Schatzle et al. | 6,425,867 B1 | 7/2002 | Vaezy |
| 5,931,805 | A | 8/1999 | Brisken | 6,425,912 B1 | 7/2002 | Knowlton |
| 5,938,606 | A | 8/1999 | Bonnefous | 6,428,477 B1 | 8/2002 | Mason |
| 5,938,612 | A | 8/1999 | Kline-Schoder | 6,428,532 B1 | 8/2002 | Doukas |
| 5,948,011 | A | 9/1999 | Knowlton | 6,430,446 B1 | 8/2002 | Knowlton |
| 5,957,844 | A | 9/1999 | Dekel | 6,432,067 B1 | 8/2002 | Martin |
| 5,957,882 | A | 9/1999 | Nita et al. | 6,432,101 B1 | 8/2002 | Weber |
| 5,967,980 | A | 10/1999 | Ferre et al. | 6,436,061 B1 | 8/2002 | Costantino |
| 5,968,034 | A | 10/1999 | Fullmer | 6,438,424 B1 | 8/2002 | Knowlton |
| 5,971,949 | A | 10/1999 | Levin | 6,440,071 B1 | 8/2002 | Slayton |
| 5,984,882 | A | 11/1999 | Rosenchein | 6,440,121 B1 | 8/2002 | Weber |
| 5,997,471 | A | 12/1999 | Gumb et al. | 6,443,914 B1 | 9/2002 | Constantino |
| 5,997,497 | A | 12/1999 | Nita et al. | 6,453,202 B1 | 9/2002 | Knowlton |
| 6,004,262 | A | 12/1999 | Putz et al. | 6,461,378 B1 | 10/2002 | Knowlton |
| 6,007,499 | A | 12/1999 | Martin et al. | 6,470,216 B1 | 10/2002 | Knowlton |
| 6,036,646 | A | 3/2000 | Barthe | 6,491,657 B2 | 12/2002 | Rowe |
| 6,039,048 | A | 3/2000 | Silberg | 6,500,121 B1 | 12/2002 | Slayton |
| 6,042,556 | A | 3/2000 | Beach | 6,500,141 B1 | 12/2002 | Irion |
| 6,049,159 | A | 4/2000 | Barthe | 6,508,774 B1 | 1/2003 | Acker |
| 6,050,943 | A | 4/2000 | Slayton | 6,511,428 B1 | 1/2003 | Azuma |
| 6,059,727 | A | 5/2000 | Fowlkes | 6,514,244 B2 | 2/2003 | Pope |
| 6,071,239 | A | 6/2000 | Cribbs | 6,524,250 B1 | 2/2003 | Weber |
| 6,080,108 | A | 6/2000 | Dunham | 6,540,679 B2 | 4/2003 | Slayton |
| 6,086,535 | A | 7/2000 | Ishibashi | 6,540,685 B1 | 4/2003 | Rhoads et al. |
| 6,086,580 | A | 7/2000 | Mordon et al. | 6,554,771 B1 | 4/2003 | Buil et al. |
| 6,090,054 | A | 7/2000 | Tagishi | 6,569,099 B1 | 5/2003 | Babaev |
| 6,093,883 | A | 7/2000 | Sanghvi | 6,595,934 B1 | 7/2003 | Hissong |
| 6,101,407 | A | 8/2000 | Groezinger | 6,599,256 B1 | 7/2003 | Acker |
| 6,106,469 | A | 8/2000 | Suzuki et al. | 6,607,498 B2 | 8/2003 | Eshel |
| 6,113,558 | A | 9/2000 | Rosenchein | 6,623,430 B1 | 9/2003 | Slayton |
| 6,113,559 | A | 9/2000 | Klopotek | 6,626,854 B2 | 9/2003 | Friedman |
| 6,120,452 | A | 9/2000 | Barthe | 6,626,855 B2 | 9/2003 | Weng |
| 6,135,971 | A | 10/2000 | Hutchinson | 6,638,226 B2 | 10/2003 | He et al. |
| 6,139,499 | A | 10/2000 | Wilk | 6,645,162 B2 | 11/2003 | Friedman |
| 6,159,150 | A | 12/2000 | Yale et al. | 6,662,054 B2 | 12/2003 | Kreindel |
| 6,171,244 | B1 | 1/2001 | Finger et al. | 6,663,627 B2 | 12/2003 | Francischelli |
| 6,176,840 | B1 | 1/2001 | Nishimura | 6,665,806 B2 | 12/2003 | Shimizu |
| 6,183,426 | B1 | 2/2001 | Akisada | 6,666,835 B2 | 12/2003 | Martin |
| 6,183,502 | B1 | 2/2001 | Takeuchi | 6,669,638 B1 | 12/2003 | Miller |
| 6,183,773 | B1 | 2/2001 | Anderson | 6,685,640 B1 | 2/2004 | Fry |
| 6,190,323 | B1 | 2/2001 | Dias | 6,692,450 B1 | 2/2004 | Coleman |
| 6,190,336 | B1 | 2/2001 | Duarte | 6,699,237 B2 | 3/2004 | Weber |
| 6,193,658 | B1 | 2/2001 | Wendelken | 6,719,449 B1 | 4/2004 | Laugharn, Jr. et al. |
| 6,210,327 | B1 | 4/2001 | Brackett et al. | 6,719,694 B2 | 4/2004 | Weng |
| 6,213,948 | B1 | 4/2001 | Barthe | 6,749,624 B2 | 6/2004 | Knowlton |
| 6,216,029 | B1 | 4/2001 | Paltieli | 6,775,404 B1 | 8/2004 | Pagoulatos et al. |
| 6,233,476 | B1 | 5/2001 | Strommer et al. | 6,824,516 B2 | 11/2004 | Batten et al. |
| 6,234,990 | B1 | 5/2001 | Rowe et al. | 6,835,940 B2 | 12/2004 | Morikawa et al. |
| 6,241,753 | B1 | 6/2001 | Knowlton | 6,875,176 B2 | 4/2005 | Mourad |
| 6,246,898 | B1 | 6/2001 | Vesely et al. | 6,887,239 B2 | 5/2005 | Elstrom |
| 6,251,088 | B1 | 6/2001 | Kaufman et al. | 6,889,089 B2 | 5/2005 | Behl |
| 6,268,405 | B1 | 7/2001 | Yao | 6,896,657 B2 | 5/2005 | Willis |
| 6,273,864 | B1 | 8/2001 | Duarte | 6,902,536 B2 | 6/2005 | Manna |
| 6,287,257 | B1 | 9/2001 | Matichuk | 6,905,466 B2 | 6/2005 | Salgo |
| 6,296,619 | B1 | 10/2001 | Brisken | 6,918,907 B2 | 7/2005 | Kelly |
| 6,301,989 | B1 | 10/2001 | Brown et al. | 6,920,883 B2 | 7/2005 | Bessette |
| 6,311,090 | B1 | 10/2001 | Knowlton | 6,921,371 B2 | 7/2005 | Wilson |
| 6,315,741 | B1 | 11/2001 | Martin | 6,932,771 B2 | 8/2005 | Whitmore |
| 6,322,509 | B1 | 11/2001 | Pan et al. | 6,936,044 B2 | 8/2005 | McDaniel |
| 6,322,532 | B1 | 11/2001 | D'Sa | 6,936,046 B2 | 8/2005 | Hissong |
| 6,325,540 | B1 | 12/2001 | Lounsberry et al. | 6,948,843 B2 | 9/2005 | Laugharn et al. |
| 6,325,769 | B1 | 12/2001 | Klopotek | 6,953,941 B2 | 10/2005 | Nakano et al. |
| 6,325,798 | B1 | 12/2001 | Edwards et al. | 6,958,043 B2 | 10/2005 | Hissong |
| 6,350,276 | B1 | 2/2002 | Knowlton | 6,974,417 B2 | 12/2005 | Lockwood |
| 6,356,780 | B1 | 3/2002 | Licato et al. | 6,976,492 B2 | 12/2005 | Ingle |
| 6,361,531 | B1 | 3/2002 | Hissong | 6,992,305 B2 | 1/2006 | Maezawa et al. |
| 6,375,672 | B1 | 4/2002 | Aksan | 6,997,923 B2 | 2/2006 | Anderson |
| 6,377,854 | B1 | 4/2002 | Knowlton | 7,006,874 B2 | 2/2006 | Knowlton |

| Patent Number | Date | Name | | Publication Number | Date | Name |
|---|---|---|---|---|---|---|
| 7,020,528 B2 | 3/2006 | Neev | | 2003/0171678 A1 | 9/2003 | Batten et al. |
| 7,022,089 B2 | 4/2006 | Ooba | | 2003/0171701 A1 | 9/2003 | Babaev |
| 7,058,440 B2 | 6/2006 | Heuscher et al. | | 2003/0176790 A1 | 9/2003 | Slayton |
| 7,063,666 B2 | 6/2006 | Weng | | 2003/0191396 A1 | 10/2003 | Sanghvi |
| 7,070,565 B2 | 7/2006 | Vaezy et al. | | 2003/0200481 A1 | 10/2003 | Stanley |
| 7,074,218 B2 | 7/2006 | Washington et al. | | 2003/0212129 A1 | 11/2003 | Liu et al. |
| 7,094,252 B2 | 8/2006 | Koop | | 2003/0212351 A1 | 11/2003 | Hissong |
| 7,115,123 B2 | 10/2006 | Knowlton | | 2003/0212393 A1 | 11/2003 | Knowlton |
| 7,142,905 B2 | 11/2006 | Slayton | | 2003/0216795 A1 | 11/2003 | Harth |
| 7,179,238 B2 | 2/2007 | Hissong | | 2003/0220536 A1 | 11/2003 | Hissong |
| 7,189,230 B2 | 3/2007 | Knowlton | | 2003/0220585 A1 | 11/2003 | Hissong |
| 7,229,411 B2 | 6/2007 | Slayton | | 2003/0236487 A1 | 12/2003 | Knowlton |
| 7,235,592 B2 | 6/2007 | Muratoglu | | 2004/0000316 A1 | 1/2004 | Knowlton |
| 7,258,674 B2 | 8/2007 | Cribbs | | 2004/0001809 A1 | 1/2004 | Brisken |
| 7,273,459 B2 | 9/2007 | Desilets | | 2004/0002705 A1 | 1/2004 | Knowlton |
| 7,297,117 B2 | 11/2007 | Trucco | | 2004/0010222 A1 | 1/2004 | Nunomura et al. |
| 7,347,855 B2 | 3/2008 | Eshel | | 2004/0015106 A1 | 1/2004 | Coleman |
| RE40,403 E | 6/2008 | Cho et al. | | 2004/0030227 A1 | 2/2004 | Littrup |
| 7,393,325 B2 | 7/2008 | Barthe | | 2004/0039312 A1 | 2/2004 | Hillstead |
| 7,491,171 B2 | 2/2009 | Barthe et al. | | 2004/0039418 A1 | 2/2004 | Elstrom |
| 7,510,536 B2 | 3/2009 | Foley et al. | | 2004/0059266 A1 | 3/2004 | Fry |
| 7,530,356 B2 | 5/2009 | Slayton | | 2004/0073079 A1 | 4/2004 | Altshuler et al. |
| 7,530,958 B2 | 5/2009 | Slayton | | 2004/0073113 A1 | 4/2004 | Salgo |
| 7,571,336 B2 | 8/2009 | Barthe | | 2004/0073116 A1 | 4/2004 | Smith |
| 7,601,120 B2 | 10/2009 | Moilanen et al. | | 2004/0077977 A1 | 4/2004 | Ella et al. |
| 7,615,015 B2 | 11/2009 | Coleman | | 2004/0082857 A1 | 4/2004 | Schonenberger |
| 7,615,016 B2 | 11/2009 | Barthe | | 2004/0082859 A1 | 4/2004 | Schaer |
| 7,758,524 B2 | 7/2010 | Barthe | | 2004/0102697 A1 | 5/2004 | Evron |
| 7,824,348 B2 | 11/2010 | Barthe | | 2004/0122493 A1 | 6/2004 | Ishibashi et al. |
| 7,955,281 B2 | 6/2011 | Pedersen et al. | | 2004/0143297 A1 | 7/2004 | Ramsey |
| 8,057,389 B2 | 11/2011 | Barthe et al. | | 2004/0152982 A1 | 8/2004 | Hwang et al. |
| 8,057,465 B2 | 11/2011 | Sliwa, Jr. et al. | | 2004/0186535 A1 | 9/2004 | Knowlton |
| 8,128,618 B2 | 3/2012 | Gliklich et al. | | 2004/0206365 A1 | 10/2004 | Knowlton |
| 8,133,191 B2 | 3/2012 | Rosenberg et al. | | 2004/0210214 A1 | 10/2004 | Knowlton |
| 8,197,409 B2 | 6/2012 | Foley et al. | | 2004/0217675 A1 | 11/2004 | Desilets |
| 8,206,299 B2 | 6/2012 | Foley et al. | | 2004/0249318 A1 | 12/2004 | Tanaka |
| 8,211,017 B2 | 7/2012 | Foley et al. | | 2004/0267252 A1 | 12/2004 | Washington |
| 8,262,591 B2 | 9/2012 | Pedersen et al. | | 2005/0033201 A1 | 2/2005 | Takahashi |
| 8,273,037 B2 | 9/2012 | Kreindel et al. | | 2005/0055073 A1 | 3/2005 | Weber |
| 8,282,554 B2 | 10/2012 | Makin et al. | | 2005/0070961 A1 | 3/2005 | Maki |
| 8,333,700 B1 | 12/2012 | Barthe et al. | | 2005/0074407 A1 | 4/2005 | Smith |
| 8,366,622 B2 * | 2/2013 | Slayton et al. ............ 600/439 | | 2005/0080469 A1 | 4/2005 | Larson |
| 2001/0009997 A1 | 7/2001 | Pope | | 2005/0113689 A1 | 5/2005 | Gritzky |
| 2001/0014780 A1 | 8/2001 | Martin | | 2005/0137656 A1 | 6/2005 | Malak |
| 2001/0014819 A1 | 8/2001 | Ingle | | 2005/0143677 A1 | 6/2005 | Young et al. |
| 2001/0031922 A1 | 10/2001 | Weng | | 2005/0154313 A1 | 7/2005 | Desilets |
| 2001/0039380 A1 | 11/2001 | Larson et al. | | 2005/0154314 A1 | 7/2005 | Quistgaard |
| 2001/0041880 A1 | 11/2001 | Brisken | | 2005/0154332 A1 | 7/2005 | Zanelli |
| 2002/0000763 A1 | 1/2002 | Jones | | 2005/0154431 A1 | 7/2005 | Quistgaard |
| 2002/0040199 A1 | 4/2002 | Klopotek | | 2005/0187495 A1 | 8/2005 | Quistgaard |
| 2002/0040442 A1 | 4/2002 | Ishidera | | 2005/0191252 A1 | 9/2005 | Mitsui |
| 2002/0055702 A1 | 5/2002 | Atala | | 2005/0193451 A1 | 9/2005 | Quistgaard |
| 2002/0062077 A1 | 5/2002 | Emmenegger | | 2005/0228281 A1 | 10/2005 | Nefos |
| 2002/0062142 A1 | 5/2002 | Knowlton | | 2005/0240170 A1 | 10/2005 | Zhang et al. |
| 2002/0082528 A1 | 6/2002 | Friedman | | 2005/0256406 A1 | 11/2005 | Barthe |
| 2002/0082589 A1 | 6/2002 | Friedman | | 2005/0261584 A1 | 11/2005 | Eshel |
| 2002/0095143 A1 | 7/2002 | Key | | 2005/0267454 A1 | 12/2005 | Hissong |
| 2002/0128648 A1 | 9/2002 | Weber | | 2006/0004306 A1 | 1/2006 | Altshuler |
| 2002/0156400 A1 | 10/2002 | Babaev | | 2006/0020260 A1 | 1/2006 | Dover et al. |
| 2002/0161357 A1 | 10/2002 | Anderson | | 2006/0025756 A1 | 2/2006 | Francischelli |
| 2002/0165529 A1 | 11/2002 | Danek | | 2006/0042201 A1 | 3/2006 | Curry |
| 2002/0168049 A1 | 11/2002 | Schriever | | 2006/0058664 A1 | 3/2006 | Barthe |
| 2002/0169394 A1 | 11/2002 | Eppstein et al. | | 2006/0058707 A1 | 3/2006 | Barthe |
| 2002/0169442 A1 | 11/2002 | Neev | | 2006/0058712 A1 | 3/2006 | Altshuler et al. |
| 2002/0173721 A1 | 11/2002 | Grunwald et al. | | 2006/0074309 A1 | 4/2006 | Bonnefous |
| 2002/0193831 A1 | 12/2002 | Smith | | 2006/0074313 A1 | 4/2006 | Slayton |
| 2003/0014039 A1 | 1/2003 | Barzell et al. | | 2006/0074314 A1 | 4/2006 | Slayton |
| 2003/0018255 A1 | 1/2003 | Martin | | 2006/0074355 A1 | 4/2006 | Slayton |
| 2003/0028113 A1 | 2/2003 | Gilbert et al. | | 2006/0079816 A1 | 4/2006 | Barthe |
| 2003/0032900 A1 | 2/2003 | Ella | | 2006/0079868 A1 | 4/2006 | Makin |
| 2003/0036706 A1 | 2/2003 | Slayton | | 2006/0084891 A1 | 4/2006 | Barthe |
| 2003/0040739 A1 | 2/2003 | Koop | | 2006/0089632 A1 | 4/2006 | Barthe |
| 2003/0050678 A1 | 3/2003 | Sierra | | 2006/0089688 A1 | 4/2006 | Panescu |
| 2003/0060736 A1 | 3/2003 | Martin et al. | | 2006/0094988 A1 | 5/2006 | Tosaya |
| 2003/0065313 A1 | 4/2003 | Koop | | 2006/0111744 A1 | 5/2006 | Makin |
| 2003/0074023 A1 | 4/2003 | Kaplan | | 2006/0116671 A1 | 6/2006 | Slayton |
| 2003/0083536 A1 | 5/2003 | Eshel | | 2006/0122508 A1 | 6/2006 | Slayton |
| 2003/0097071 A1 | 5/2003 | Halmann et al. | | 2006/0122509 A1 | 6/2006 | Desilets |
| 2003/0125629 A1 | 7/2003 | Ustuner | | 2006/0161062 A1 | 7/2006 | Arditi et al. |

| | | | | | | |
|---|---|---|---|---|---|---|
| 2006/0184069 A1 | 8/2006 | Vaitekunas | | EP | 1234566 | 8/2002 |
| 2006/0184071 A1 | 8/2006 | Klopotek | | EP | 1262160 | 12/2002 |
| 2006/0206105 A1 | 9/2006 | Chopra | | GB | 2113099 | 8/1983 |
| 2006/0229514 A1 | 10/2006 | Wiener | | JP | 63036171 | 2/1988 |
| 2006/0241440 A1 | 10/2006 | Eshel | | JP | 03048299 | 3/1991 |
| 2006/0241442 A1 | 10/2006 | Barthe | | JP | 3123559 | 5/1991 |
| 2006/0250046 A1 | 11/2006 | Koizumi et al. | | JP | 03136642 | 6/1991 |
| 2006/0261584 A1 | 11/2006 | Blackburn | | JP | 4089058 | 3/1992 |
| 2006/0282691 A1 | 12/2006 | Barthe | | JP | 4-150847 | 5/1992 |
| 2006/0291710 A1 | 12/2006 | Wang et al. | | JP | 7080087 | 3/1995 |
| 2007/0032784 A1 | 2/2007 | Gliklich | | JP | 07505793 | 6/1995 |
| 2007/0035201 A1 | 2/2007 | Desilets | | JP | 7222782 | 8/1995 |
| 2007/0055154 A1 | 3/2007 | Torbati | | JP | 11-505440 | 5/1999 |
| 2007/0055156 A1 | 3/2007 | Desilets | | JP | 11-506636 | 6/1999 |
| 2007/0087060 A1 | 4/2007 | Dietrich | | JP | 2000166940 | 6/2000 |
| 2007/0088346 A1 | 4/2007 | Mirizzi et al. | | JP | 2001170068 | 6/2001 |
| 2007/0167709 A1 | 7/2007 | Slayton | | JP | 2002078764 | 3/2002 |
| 2007/0208253 A1 | 9/2007 | Slayton | | JP | 2002515786 | 5/2002 |
| 2007/0239075 A1 | 10/2007 | Rosenberg | | JP | 2002521118 | 7/2002 |
| 2008/0027328 A1 | 1/2008 | Klopotek | | JP | 2002-537939 | 11/2002 |
| 2008/0071255 A1 | 3/2008 | Barthe | | JP | 2003050298 | 2/2003 |
| 2008/0086054 A1 | 4/2008 | Slayton | | JP | 2003204982 | 7/2003 |
| 2008/0097253 A1 | 4/2008 | Pedersen et al. | | JP | 2004-147719 | 5/2004 |
| 2008/0167556 A1 | 7/2008 | Thompson | | JP | 2005503388 | 2/2005 |
| 2008/0200813 A1 | 8/2008 | Quistgaard | | JP | 2005527336 | 9/2005 |
| 2008/0214966 A1 | 9/2008 | Slayton | | JP | 2005323213 | 11/2005 |
| 2008/0221491 A1 | 9/2008 | Slayton | | JP | 2006520247 | 9/2006 |
| 2008/0275342 A1 | 11/2008 | Barthe | | JP | 2009518126 | 5/2009 |
| 2008/0281237 A1 | 11/2008 | Slayton | | JP | 2010517695 | 5/2010 |
| 2008/0281255 A1 | 11/2008 | Slayton | | KR | 1020010024871 | 3/2001 |
| 2008/0294073 A1 | 11/2008 | Barthe | | KR | 1020060113930 | 11/2006 |
| 2008/0319356 A1 | 12/2008 | Cain | | KR | 1020070065332 | 6/2007 |
| 2009/0069677 A1 | 3/2009 | Chen et al. | | KR | 1020070070161 | 7/2007 |
| 2009/0182231 A1 | 7/2009 | Barthe et al. | | KR | 1020070098856 | 10/2007 |
| 2009/0216159 A1 | 8/2009 | Slayton et al. | | KR | 1020070104878 | 10/2007 |
| 2009/0226424 A1 | 9/2009 | Hsu | | KR | 1020070114105 | 11/2007 |
| 2009/0253988 A1 | 10/2009 | Slayton et al. | | WO | WO 96/25888 | 8/1996 |
| 2009/0318909 A1 | 12/2009 | Debenedictis et al. | | WO | WO 9735518 | 10/1997 |
| 2010/0011236 A1 | 1/2010 | Barthe et al. | | WO | WO 9832379 | 7/1998 |
| 2010/0022922 A1 | 1/2010 | Barthe et al. | | WO | WO 9933520 | 7/1999 |
| 2010/0160782 A1 | 6/2010 | Slayton et al. | | WO | WO 9949788 | 10/1999 |
| 2010/0241035 A1 | 9/2010 | Barthe et al. | | WO | WO 0006032 | 2/2000 |
| 2010/0280420 A1 | 11/2010 | Barthe et al. | | WO | WO 0015300 | 3/2000 |
| 2011/0112405 A1 | 5/2011 | Barthe et al. | | WO | WO 0021612 | 4/2000 |
| 2011/0178444 A1 | 7/2011 | Slayton et al. | | WO | WO 0053113 | 9/2000 |
| 2012/0016239 A1 | 1/2012 | Barthe et al. | | WO | WO 0128623 | 4/2001 |
| 2012/0029353 A1 | 2/2012 | Slayton et al. | | WO | WO 0182777 | 11/2001 |
| 2012/0035475 A1 | 2/2012 | Barthe et al. | | WO | WO 0182778 | 11/2001 |
| 2012/0035476 A1 | 2/2012 | Barthe et al. | | WO | WO 0187161 | 11/2001 |
| 2012/0046547 A1 | 2/2012 | Barthe et al. | | WO | WO 0209813 | 2/2002 |
| 2012/0053458 A1 | 3/2012 | Barthe et al. | | WO | WO 0224050 | 3/2002 |
| 2012/0111339 A1 | 5/2012 | Barthe et al. | | WO | WO 02092168 | 11/2002 |
| 2012/0143056 A1 | 6/2012 | Slayton et al. | | WO | WO 03065347 | 8/2003 |
| 2012/0165668 A1 | 6/2012 | Slayton et al. | | WO | WO 03070105 | 8/2003 |
| 2012/0165848 A1 | 6/2012 | Slayton et al. | | WO | WO 03077833 | 9/2003 |
| 2012/0197120 A1 | 8/2012 | Makin et al. | | WO | WO 03086215 | 10/2003 |
| 2012/0197121 A1 | 8/2012 | Slayton et al. | | WO | WO 03/096883 A2 | 11/2003 |
| 2012/0215105 A1 | 8/2012 | Slayton et al. | | WO | WO 03099177 | 12/2003 |
| 2012/0271294 A1* | 10/2012 | Barthe et al. ............ 606/28 | | WO | WO 03101530 | 12/2003 |
| 2012/0330197 A1 | 12/2012 | Makin et al. | | WO | WO 2004080147 | 9/2004 |
| 2012/0330222 A1 | 12/2012 | Makin et al. | | WO | WO 2004110558 | 12/2004 |
| 2012/0330223 A1 | 12/2012 | Makin et al. | | WO | WO 2005065408 | 7/2005 |
| 2013/0012755 A1 | 1/2013 | Slayton | | WO | WO 2005090978 | 9/2005 |
| 2013/0012816 A1 | 1/2013 | Slayton et al. | | WO | WO 2006036870 | 4/2006 |
| 2013/0012838 A1 | 1/2013 | Jaeger et al. | | WO | WO 2006042168 | 4/2006 |
| 2013/0018286 A1 | 1/2013 | Slayton et al. | | WO | WO 2006042201 | 4/2006 |
| 2013/0046209 A1 | 2/2013 | Slayton et al. | | WO | WO 2006065671 | 6/2006 |
| 2013/0066208 A1 | 3/2013 | Barthe et al. | | WO | WO 2006082573 | 8/2006 |
| 2013/0072826 A1 | 3/2013 | Slayton et al. | | WO | WO2009013729 | 1/2009 |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 A2 | 12/1989 |
| EP | 1479412 A1 | 11/1991 |
| EP | 0473553 | 4/1992 |
| EP | 0661029 A1 | 7/1995 |
| EP | 1050322 A1 | 11/2000 |

OTHER PUBLICATIONS

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Chen, L. et al., "Effect of Blood Perfusion on the ablation of liver parenchyma with high intensity focused ultrasound," Phys. Med. Biol; 38:1661-1673; 1993b.

Coon, Joshua et al., "Protein identification using sequential ion/ion reactions and tandem mass spectometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Damianou et al., "Application of the Thermal Dose Concept for Predicting the Necrosed Tissue Volume During Ultrasound Surgery," 1993 IEEE Ultrasound Symposium, pp. 1199-1202.

Daum et al., Design and Evaluation of a Feedback Based Phased Array System for Ultrasound Surgery, IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Fry, W.J. et al., "Production of Focal Destructive Lesions in the Central Nervous System with Ultrasound," J. Neurosurg., 11:471-478; 1954.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.

Harr, G.R. et al., "Tissue Destruction with Focused Ultrasound in Vivo," Eur. Urol. 23 (suppl. 1):8-11; 1993.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-Instrusive Measurement of Microwave and Ultrasound-Induced Hyperthermia by Acoustic Temperature Tomography", Ultrasonics Symposium Proceedings, pp. 977-982. (1977).

Madersbacher, S. et al., "Tissue Ablation in Bening Prostatic Hyperplasia with High Intensity Focused Ultrasound," Dur. Urol., 23 (suppl. 1):39-43; 1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmed Bulk Ablation and Therapy Monitoring Using Intracorporeal Image-Treat Ultrasound Arrays," 4th International Symposium on Theraputic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Mitragotri, S., "Healing sound: the use of ultrasound in drug delivery and other therapeutic applications," Nature Reviews; Drug Delivery, pp. 255-260, vol. 4 (Mar. 2005).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostate Tissue Using Focused Ultrasound," 1993 Ultrasonics Symposium, IEEE, pp. 1207-1210.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Termometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.

\* cited by examiner

ULTRASOUND TREATMENT OF SUB-DERMAL TISSUE FOR COSMETIC EFFECTS

CROSS-REFERENCE TO RELATED APPLICATIONS

This application is a continuation of U.S. application Ser. No. 13/444,336, now U.S. Pat. No. 8,366,622, titled "Treatment Of Sub-Dermal Regions For Cosmetic Effects" filed on Apr. 11, 2012, which is a continuation of U.S. application Ser. No. 11/163,151 titled "Method And System For Noninvasive Face Lifts And Deep Tissue Tightening" filed on Oct. 6, 2005, now abandoned, which claims the benefit of priority to U.S. Provisional Application No. 60/616,755, titled "Method And System For Noninvasive Face Lifts And Deep Tissue Tightening" filed on Oct. 6, 2004, each of which is incorporated in its entirety by reference herein.

BACKGROUND

1. Field of the Invention

The present invention relates to ultrasound therapy and imaging systems, and in particular to a method and system for noninvasive face lifts and deep tissue tightening.

2. Description of the Related Art

Coarse sagging of the skin and facial musculature occurs gradually over time due to gravity and chronic changes in connective tissue generally associated with aging. Invasive surgical treatment to tighten such tissues is common, for example by facelift procedures. In these treatments for connective tissue sagging, a portion of the tissue is usually removed, and sutures or other fasteners are used to suspend the sagging tissue structures. On the face, the Superficial Muscular Aponeurosis System (SMAS) forms a continuous layer superficial to the muscles of facial expression and beneath the skin and subcutaneous fat. Conventional face lift operations involve suspension of the SMAS through such suture and fastener procedures.

No present procedures have been developed yet, which provide the combination of targeted, precise, local heating to a specified temperature region capable of inducing ablation (thermal injury) to underlying skin and subcutaneous fat. Attempts have included the use of radio frequency (RF) devices that have been used to produce heating and shrinkage of skin on the face with some limited success as a noninvasive alternative to surgical lifting procedures. However, RF is a dispersive form of energy deposition. RF energy is impossible to control precisely within the heated tissue volume and depth, because resistive heating of tissues by RF energy occurs along the entire path of electrical conduction through tissues. Another restriction of RF energy for non-invasive tightening of the SMAS is unwanted destruction of the overlying fat and skin layers. The electric impedance to RF within fat, overlying the suspensory connective structures intended for shrinking, leads to higher temperatures in the fat than in the target suspensory structures. Similarly, mid-infrared lasers and other light sources have been used to non-invasively heat and shrink connective tissues of the dermis, again with limited success. However, light is not capable of non-invasive treatment of SMAS because light does not penetrate deeply enough to produce local heating there. Below a depth of approximately 1 mm, light energy is multiply scattered and cannot be focused to achieve precise local heating.

SUMMARY OF THE INVENTION

A method and system for noninvasive face lifts and deep tissue tightening are provided. An exemplary method and treatment system are configured for the imaging, monitoring, and thermal injury to treat the SMAS region. In accordance with an exemplary embodiment, the exemplary method and system are configured for treating the SMAS region by first, imaging of the region of interest for localization of the treatment area and surrounding structures, second, delivery of ultrasound energy at a depth, distribution, timing, and energy level to achieve the desired therapeutic effect, and third to monitor the treatment area before, during, and after therapy to plan and assess the results and/or provide feedback.

In accordance with an exemplary embodiment, an exemplary treatment system comprises an imaging/therapy probe, a control system and display system. The imaging/therapy probe can comprise various probe and/or transducer configurations. For example, the probe can be configured for a combined dual-mode imaging/therapy transducer, coupled or co-housed imaging/therapy transducers, or simply a therapy probe and an imaging probe. The control system and display system can also comprise various configurations for controlling probe and system functionality, including for example a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

In accordance with an exemplary embodiment, ultrasound imaging can be utilized for safety purposes, such as to avoid injuring vital structures such as the facial nerve (motor nerve), parotid gland, facial artery, and trigeminal nerve (for sensory functions) among others. For example, ultrasound imaging can be used to identify SMAS as the superficial layer well defined by echoes overlying the facial muscles. Such muscles can be readily seen and better identified by moving them, and their image may be further enhanced via signal and image processing.

In accordance with an exemplary embodiment, ultrasound therapy via focused ultrasound, an array of foci, a locus of foci, a line focus, and/or diffraction patterns from single element, multiple elements, annular array, one-, two-, or three-dimensional arrays, broadband transducers, and/or combinations thereof, with or without lenses, acoustic components, mechanical and/or electronic focusing are utilized to treat the SMAS region at fixed and/or variable depth or dynamically controllable depths and positions.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a method and system for noninvasive face lift and deep tissue tightening as described herein are merely indicative of exemplary applications for the invention. For example, the principles, features and methods discussed may be applied to any SMAS-like muscular fascia, such as platysma, temporal fascia, and/or occipital fascia, or any other medical application. Further, various aspects of the present invention may be suitably applied to other applications.

Figure 1:
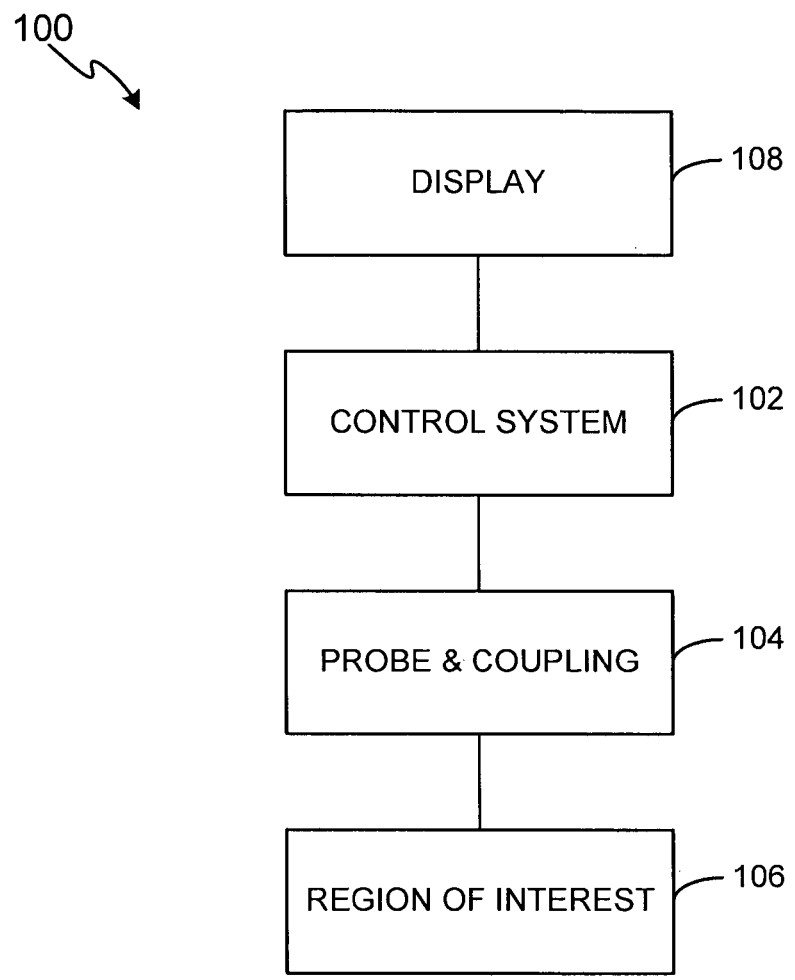
FIG. 1 illustrates a block diagram of a treatment system in accordance with an exemplary embodiment of the present invention.

In accordance with various aspects of the present invention, a method and system for noninvasive face lifts and deep tissue tightening are provided. For example, in accordance with an exemplary embodiment, with reference to FIG. 1, an exemplary treatment system 100 configured to treat a region of interest 106 comprises a control system 102, an imaging/therapy probe with acoustic coupling 104, and a display system 108. Control system 102 and display system 108 can comprise various configurations for controlling probe 102 and overall system 100 functionality, such as, for example, a microprocessor with software and a plurality of input/output devices, system and devices for controlling electronic and/or mechanical scanning and/or multiplexing of transducers, a system for power delivery, systems for monitoring, systems for sensing the spatial position of the probe and/or transducers, and/or systems for handling user input and recording treatment results, among others. Imaging/therapy probe 104 can comprise various probe and/or transducer configurations. For example, probe 104 can be configured for a combined dual-mode imaging/therapy transducer, coupled or co-housed imaging/therapy transducers, or simply a separate therapy probe and an imaging probe.

In accordance with an exemplary embodiment, treatment system 100 is configured for treating the SMAS region by first, imaging of region of interest 106 for localization of the treatment area and surrounding structures, second, delivery of ultrasound energy at a depth, distribution, timing, and energy level to achieve the desired therapeutic effect, and third to monitor the treatment area before, during, and after therapy to plan and assess the results and/or provide feedback.

As to the treatment of the SMAS region, connective tissue can be permanently tightened by thermal treatment to temperatures about 60 degrees C. or higher. Upon ablating, collagen fibers shrink immediately by approximately 30% of their length. The shrunken fibers can produce tightening of the tissue, wherein the shrinkage should occur along the dominant direction of the collagen fibers. Throughout the body, collagen fibers are laid down in connective tissues along the lines of chronic stress (tension). On the aged face, the collagen fibers of the SMAS region are predominantly oriented along the lines of gravitational tension. Shrinkage of these fibers results in tightening of the SMAS in the direction desired for correction of laxity and sagging due to aging. The treatment comprises the ablation of specific regions of the SMAS region and similar suspensory connective tissues.

In addition, the SMAS region varies in depth and thickness at different locations, e.g., between 0.5 mm to 5 mm or more. On the face, important structures such as nerves, parotid gland, arteries and veins are present over, under or near the SMAS region. Tightening of the SMAS in certain locations, such as the preauricular region associated with sagging of the cheek to create jowls, the frontal region to associated with sagging brows, mandibular region associated with sagging neck, can be conducted. Treating through localized heating of regions of the SMAS or other suspensory subcutaneous connective tissue structures to temperatures of about 60-90° C., without significant damage to overlying or distal/underlying tissue, i.e., proximal tissue, as well as the precise delivery of therapeutic energy to SMAS regions, and obtaining feedback from the region of interest before, during, and after treatment can be suitably accomplished through treatment system 100.

To further illustrate an exemplary method and system 200, with reference to FIG. 2, imaging of a region of interest 206, such as by imaging a region 222 and displaying images 224 of the region of interest 206 on a display 208, to facilitate localization of the treatment area and surrounding structures can initially be conducted. Next, delivery of ultrasound energy 220 at a suitably depth, distribution, timing, and energy level to achieve the desired therapeutic effect of thermal injury or ablation to treat SMAS region 216 can be suitably provided by probe 204 through control by control system 202. Monitoring of the treatment area and surrounding structures before, during, and after therapy, i.e., before, during, and after the delivery of ultrasound energy to SMAS region 216, can be provided to plan and assess the results and/or provide feedback to control system 202 and a system user.

Ultrasound imaging and providing of images 224 can facilitate safe targeting of the SMAS layer 216. For example, with reference to FIG. 2B, specific targeting for the delivery of energy can be better facilitated to avoid heating vital structures such as the facial nerve (motor nerve) 234, parotid gland (which makes saliva) 236, facial artery 238, and trigeminal nerve (for sensory functions) 232 among other regions. Further, use of imaging with targeted energy delivery to provide a limited and controlled depth of treatment can minimize the chance of damaging deep structures, such as for example, the facial nerve that lies below the parotid, which is typically 10 mm thick.

Figure 2A:
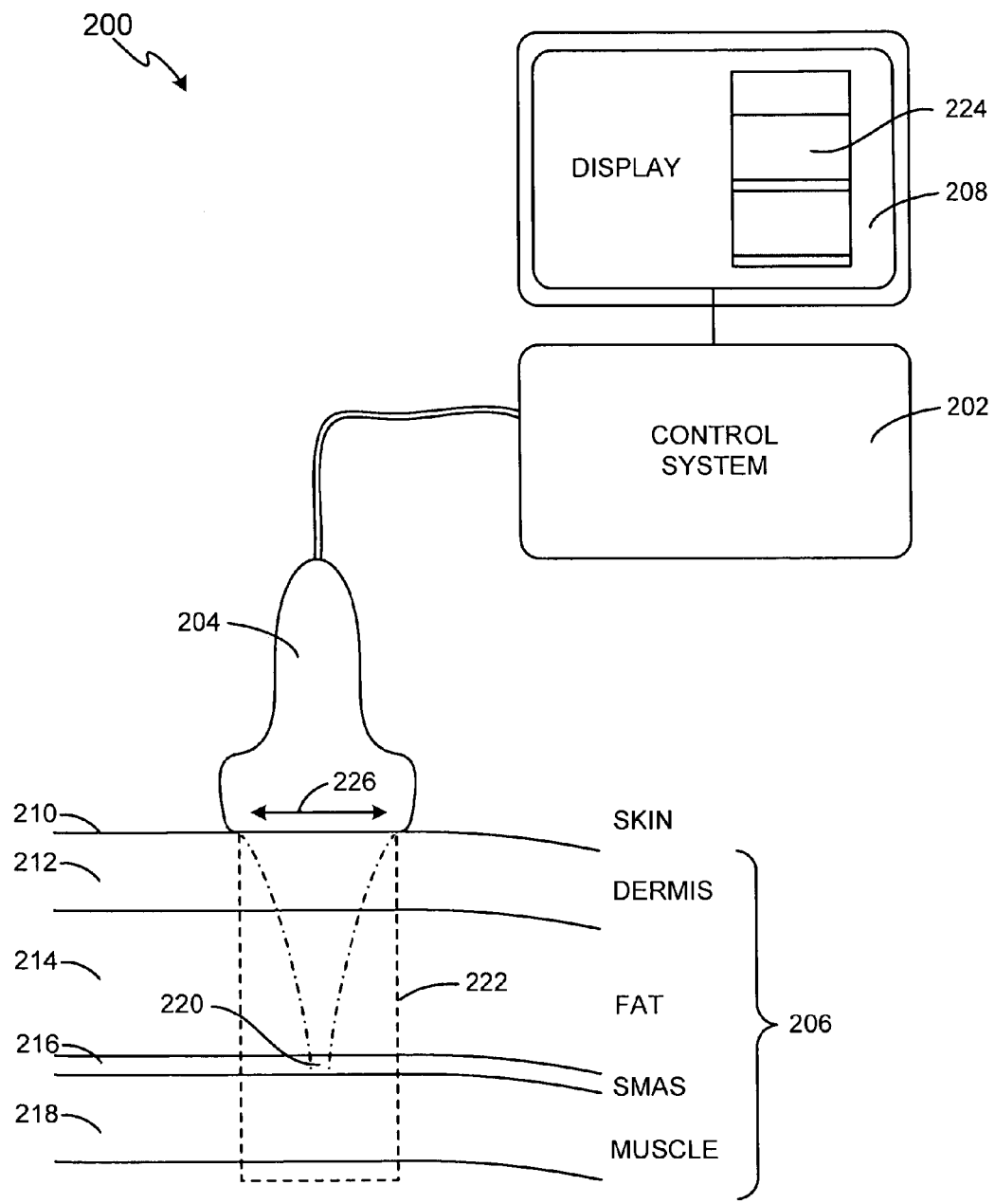
FIGS. 2A-2F illustrates schematic diagrams of an ultrasound imaging/therapy and monitoring system for treating the SMAS layer in accordance with various exemplary embodiments of the present invention.
Figure 2B:
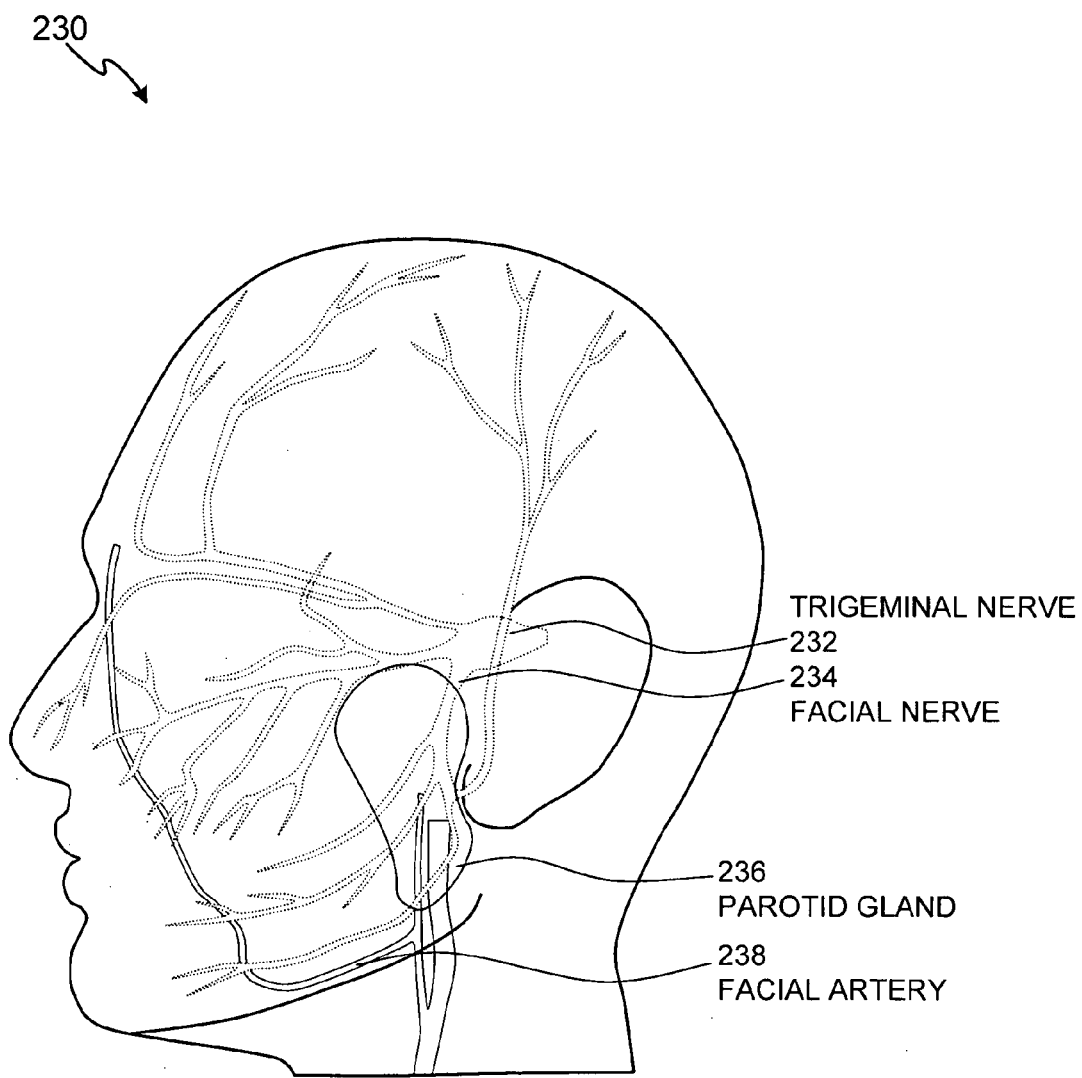
Figure 2C:
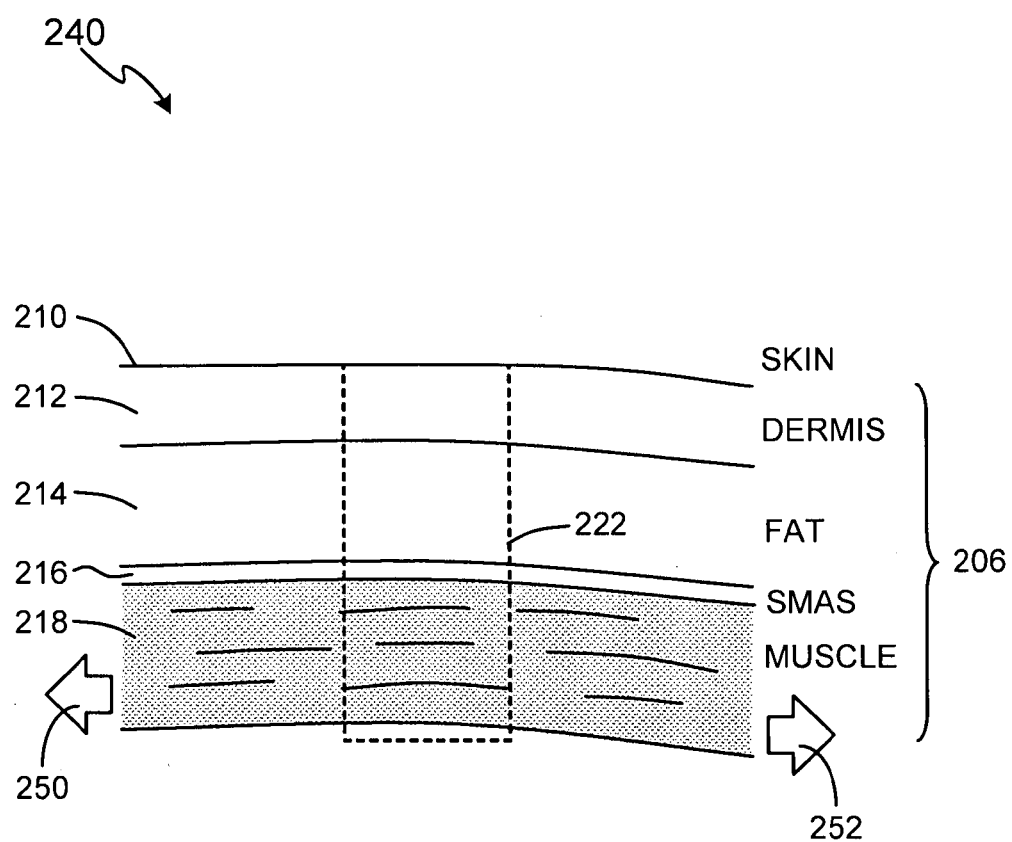

In accordance with an exemplary embodiment, with reference to FIG. 2C, ultrasound imaging of region 222 of the region of interest 206 can also be used to delineate SMAS layer 216 as the superficial, echo-dense layer overlying facial muscles 218. Such muscles can be seen via imaging region 222 by moving muscles 218, for example by extensional flexing of muscle layer 218 generally towards directions 250 and 252. Such imaging of region 222 may be further enhanced via signal and image processing. Once SMAS layer 216 is localized and/or identified, SMAS layer 216 is ready for treatment.

The delivery of ultrasound energy 220 at a suitably depth, distribution, timing, and energy level is provided by probe 204 through controlled operation by control system 202 to achieve the desired therapeutic effect of thermal injury to treat SMAS region 216. During operation, probe 204 can also be mechanically and/or electronically scanned within tissue surface region 226 to treat an extended area. In addition, spatial control of a treatment depth 220 can be suitably adjusted in various ranges, such as between a wide range of approximately 0 to 15 mm, suitably fixed to a few discrete depths, with an adjustment limited to a fine range, e.g. approximately between 3 mm to 9 mm, and/or dynamically adjusted during treatment, to treat SMAS layer 216 that typically lies at a depth between approximately 5 mm to 7 mm. Before, during, and after the delivery of ultrasound energy to SMAS region 216, monitoring of the treatment area and surrounding structures can be provided to plan and assess the results and/or provide feedback to control system 202 and a system user.

Figure 2D:
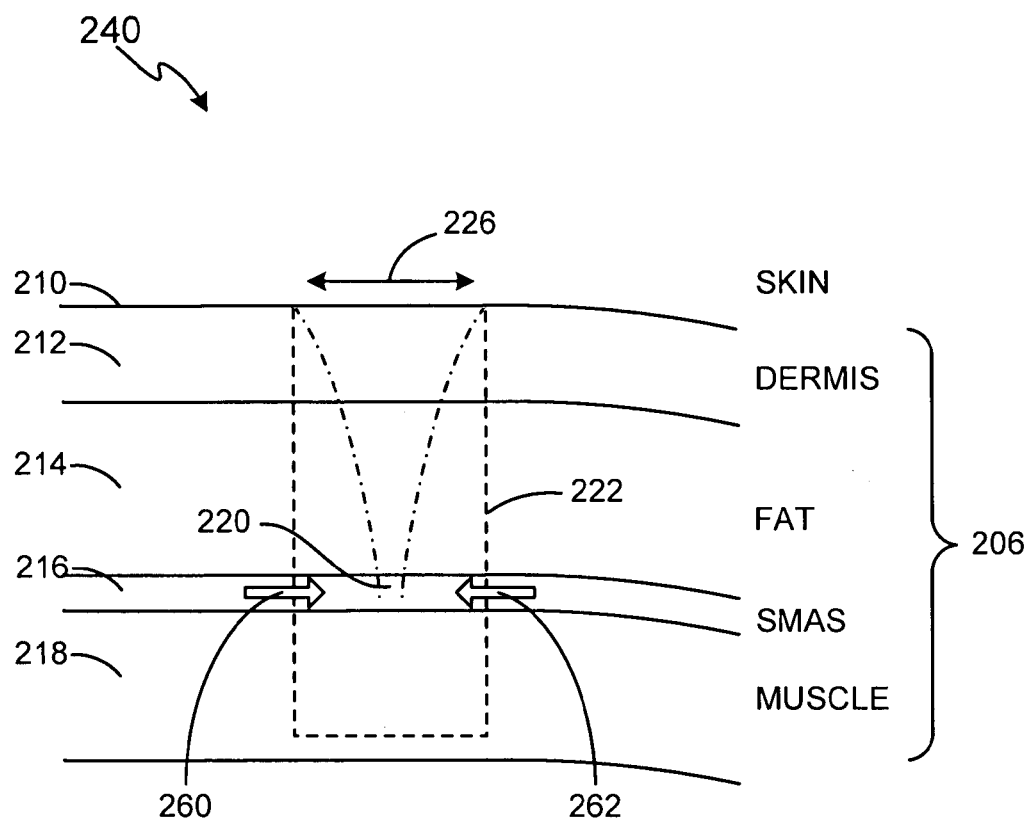

For example, in accordance with an exemplary embodiment, with additional reference to FIG. 2D, ultrasound imaging of region 222 can be used to monitor treatment by watching the amount of shrinkage of SMAS layer 216 in direction of areas 260 and 262, such as in real time or quasi-real time, during and after energy delivery to region 220. The onset of substantially immediate shrinkage of SMAS layer 216 is detectable by ultrasound imaging of region 222 and may be further enhanced via image and signal processing. The monitoring of such shrinkage can be ideal because it can confirm the intended therapeutic goal of noninvasive lifting and tissue tightening; in addition, such monitoring may be used for system feedback. In addition to image monitoring, additional treatment parameters that can be suitably monitored in accordance with various other exemplary embodiments may include temperature, video, profilometry, strain imaging and/or gauges or any other suitable spatial, temporal and/or other tissue parameters.

Figure 2E:
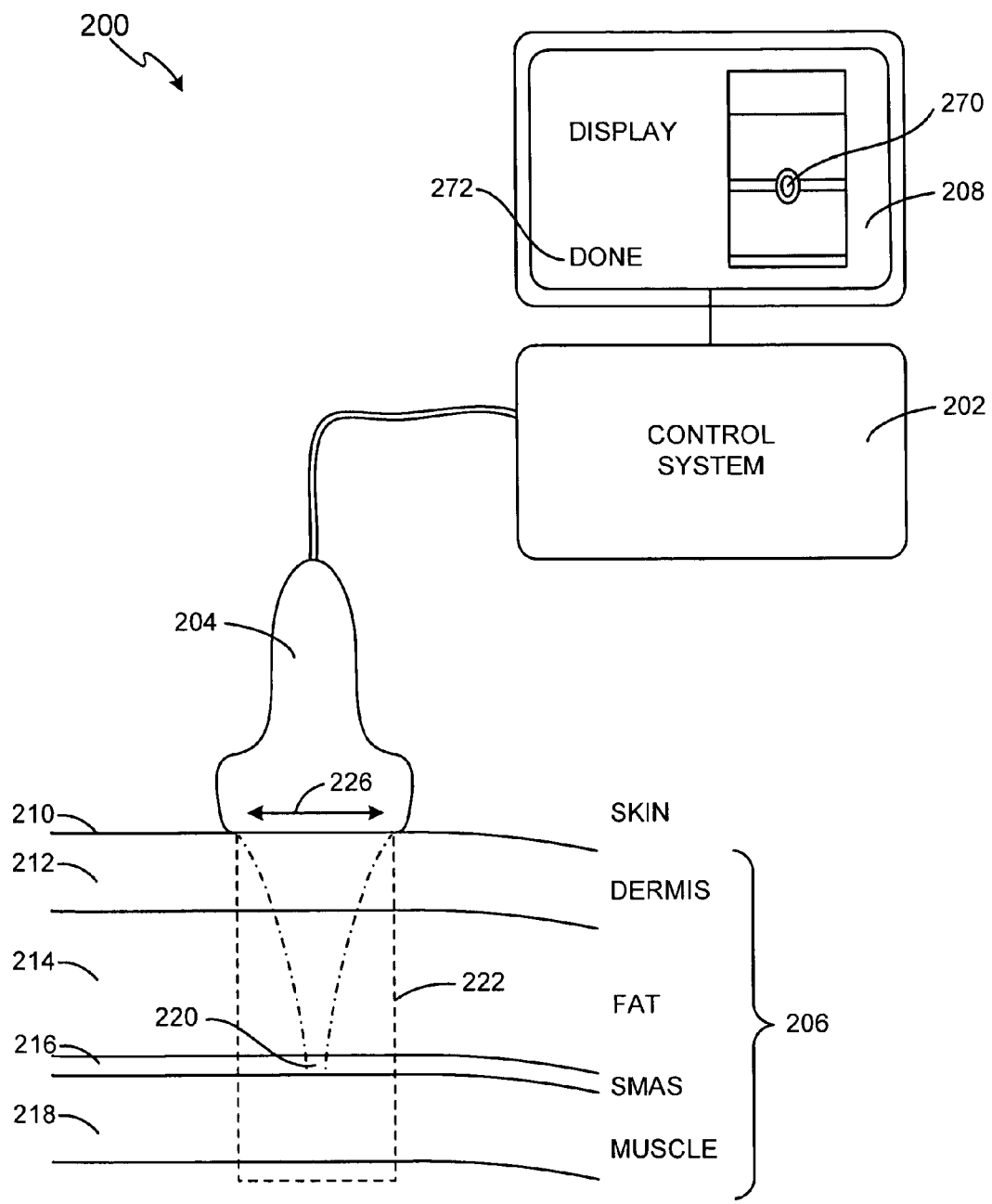

For example, in accordance with an exemplary embodiment of the present invention, with additional reference to FIG. 2E, an exemplary monitoring method and system 200 may suitably monitor the temperature profile or other tissue parameters of the region of interest 206, such as attenuation or speed of sound of treatment region 222 and suitably adjust the spatial and/or temporal characteristics and energy levels of ultrasound therapy transducer probe 204. The results of such monitoring techniques may be indicated on display 208 in various manners, such as, for example, by way of one-, two-, or three-dimensional images of monitoring results 270, or may comprise an indicator 272, such as a success, fail and/or completed/done type of indication, or combinations thereof.

Figure 2F:
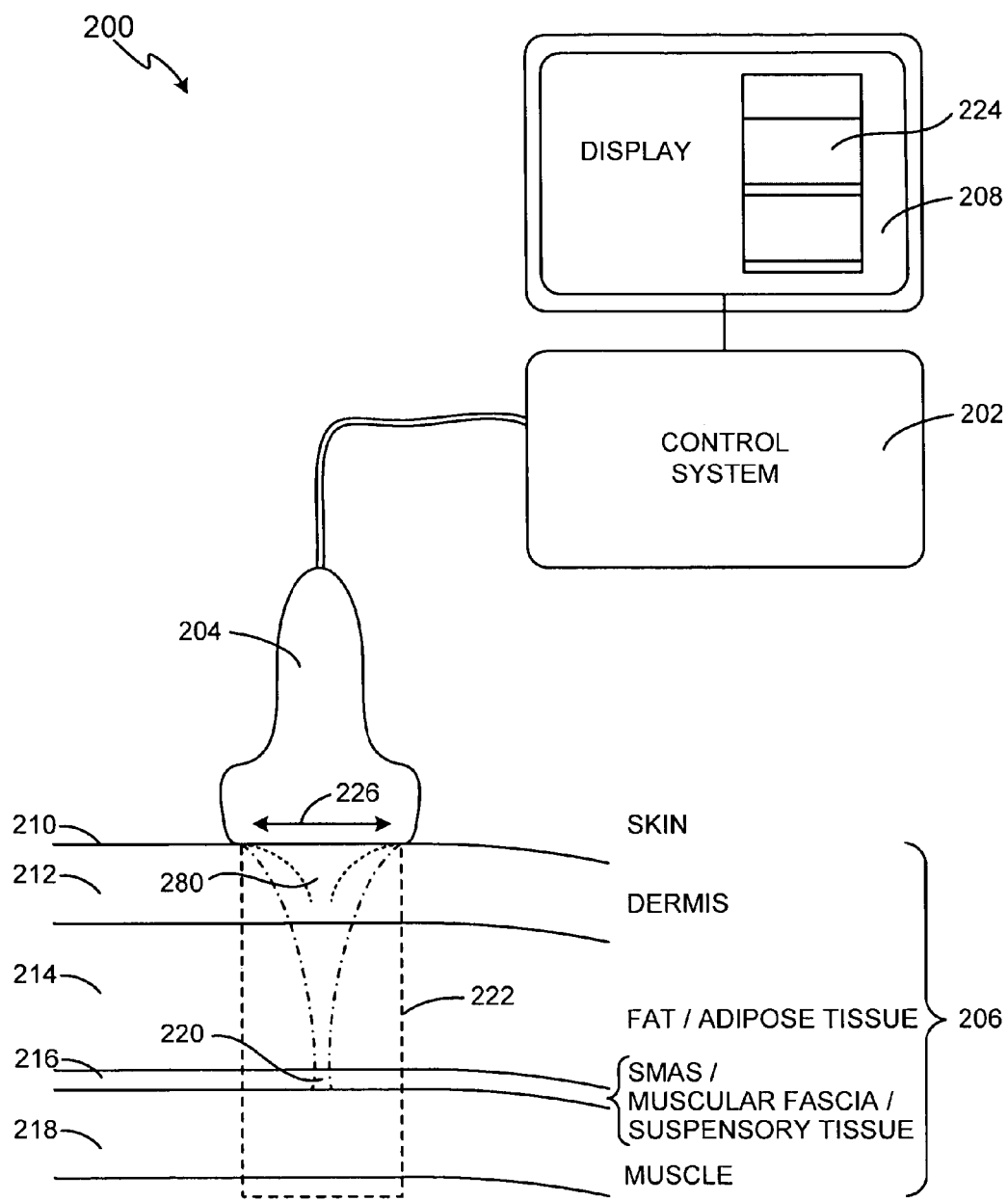

In accordance with another exemplary embodiment, with reference to FIG. 2F, the targeting of particular region 220 within SMAS layer 216 can be suitably be expanded within region of interest 206 to include a combination of tissues, such as skin 210, dermis 212, fat/adipose tissue 214, SMAS/muscular fascia/and/or other suspensory tissue 216, and muscle 218. Treatment of a combination of such tissues and/or fascia may be treated including at least one of SMAS layer 216 or other layers of muscular fascia in combination with at least one of muscle tissue, adipose tissue, SMAS and/or other muscular fascia, skin, and dermis, can be suitably achieved by treatment system 200. For example, treatment of SMAS layer 216 may be performed in combination with treatment of dermis 280 by suitable adjustment of the spatial and temporal parameters of probe 204 within treatment system 200.

Figure 3A:
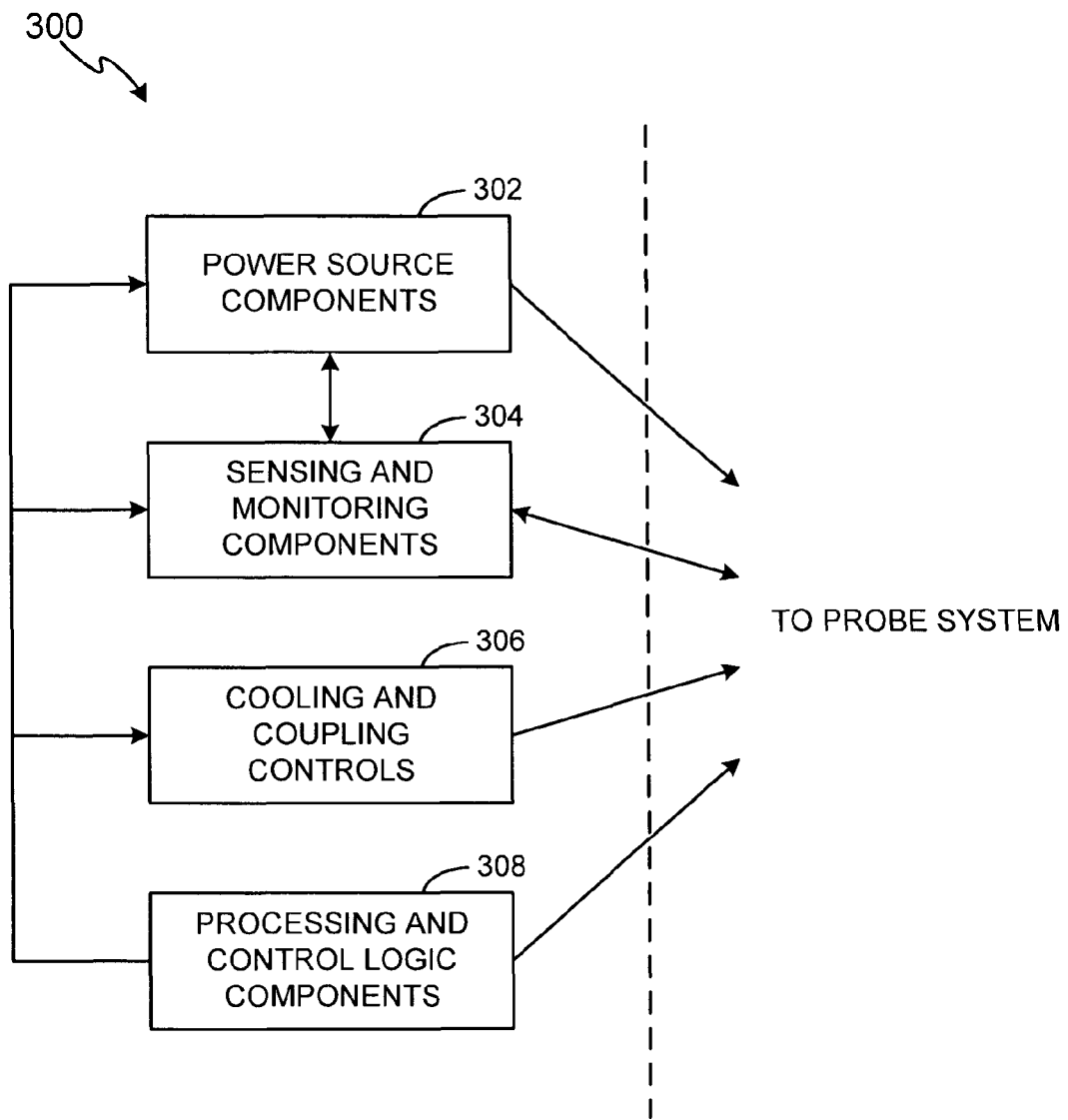
FIGS. 3A and 3B illustrate block diagrams of an exemplary control system in accordance with exemplary embodiments of the present invention.
Figure 3B:
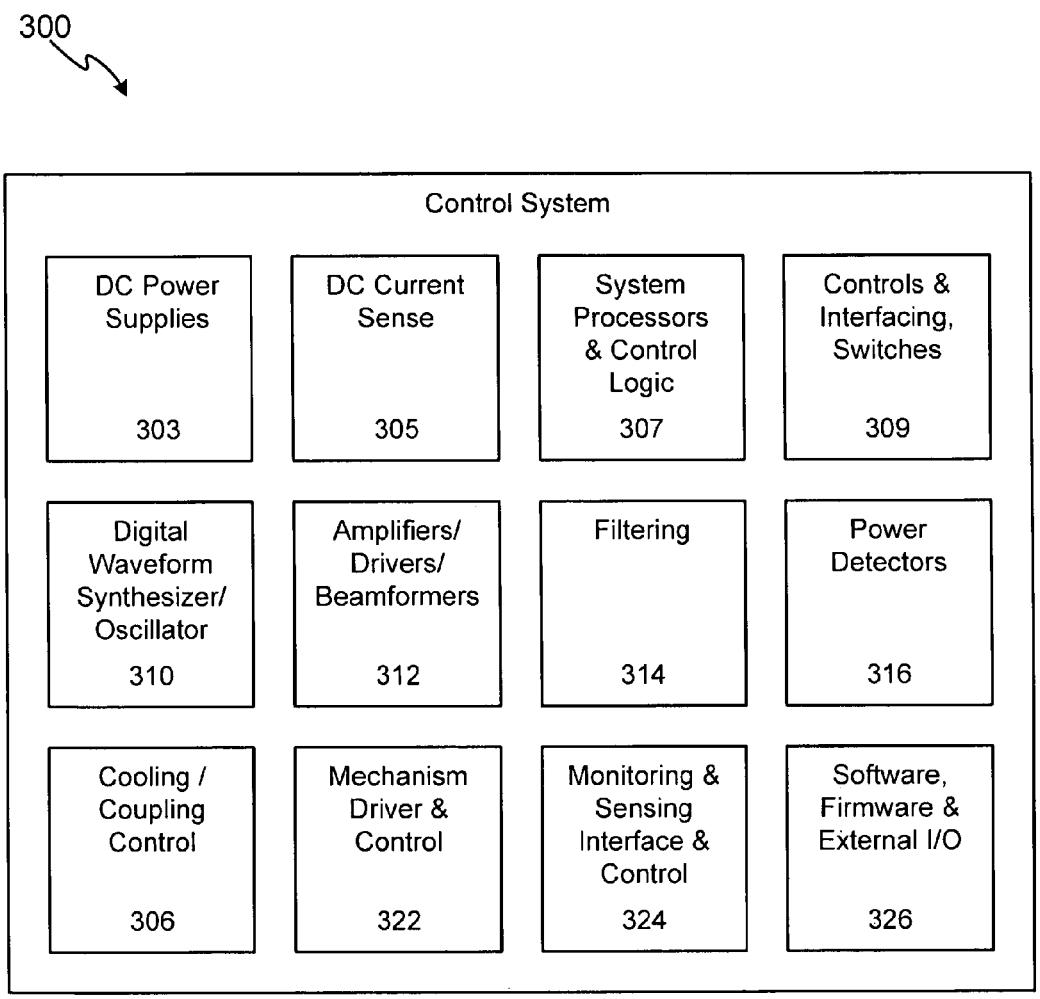

An exemplary control system 202 and display system 208 may be configured in various manners for controlling probe and system functionality. With reference to FIGS. 3A and 3B, in accordance with exemplary embodiments, an exemplary control system 300 can be configured for coordination and control of the entire therapeutic treatment process for noninvasive face lifts and deep tissue tightening. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments. Moreover, the therapy contemplated herein can also be produced, for example, by transducers disclosed in U.S. application Ser. No. 10/944,499, filed on Sep. 16, 2004, entitled Method And System For Ultrasound Treatment With A Multi-Directional Transducer and U.S. application Ser. No. 10/944,500, filed on Sep. 16, 2004, and entitled System And Method For Variable Depth Ultrasound Treatment, both hereby incorporated by reference.

Figure 4A:
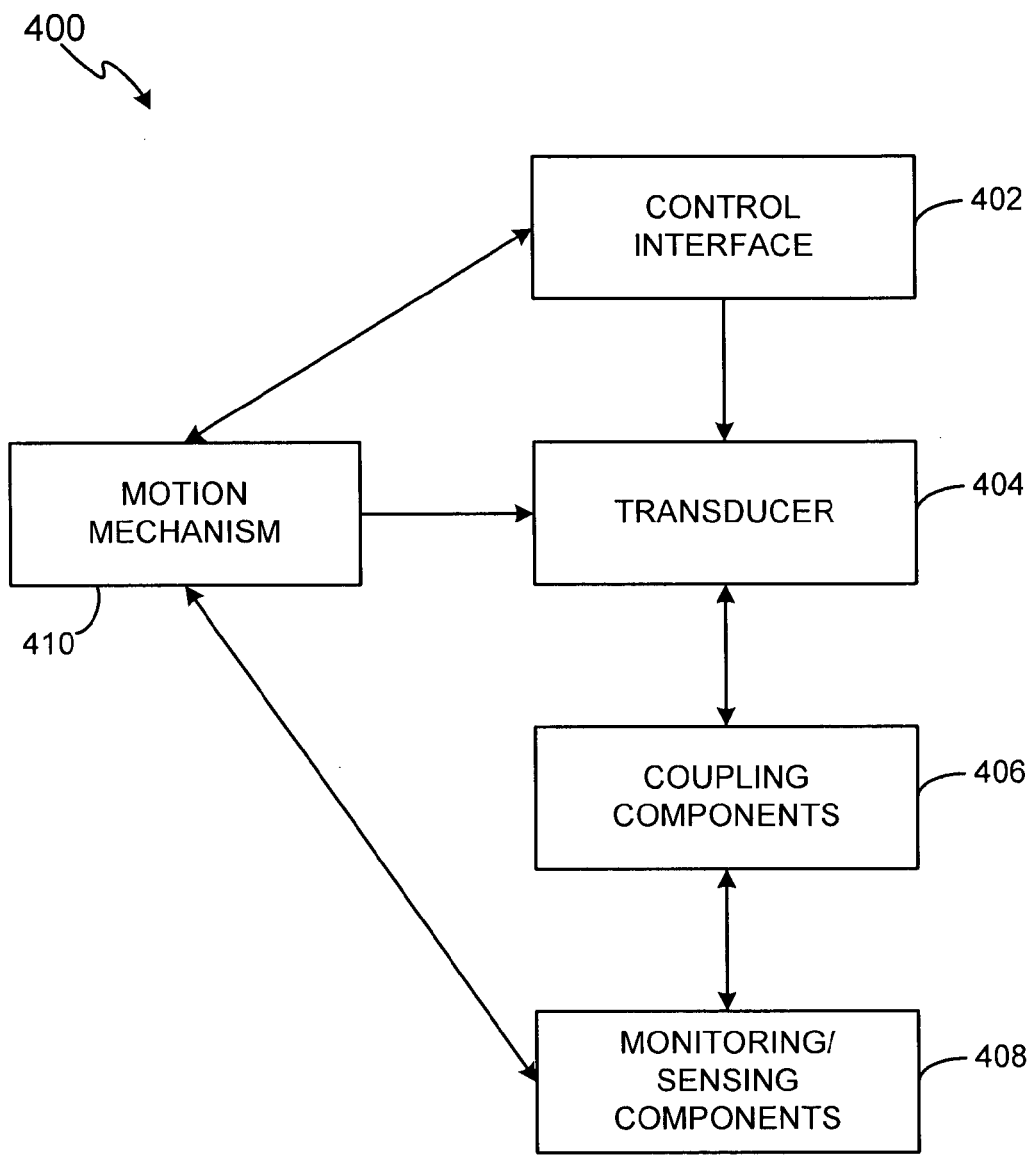
FIGS. 4A and 4B illustrate block diagrams of an exemplary probe system in accordance with exemplary embodiments of the present invention.
Figure 4B:
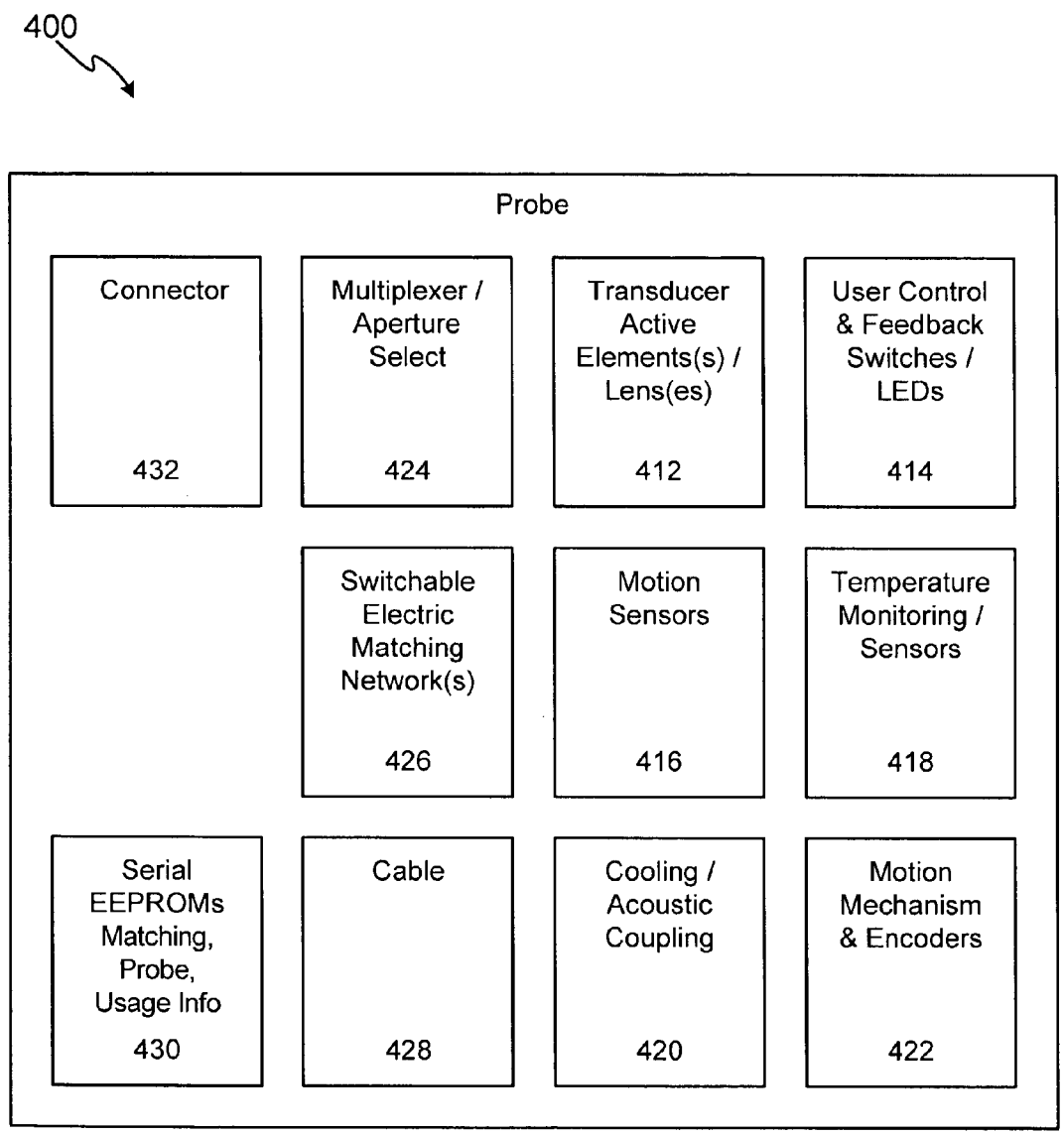

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide ultrasound energy for controlled thermal injury, and the embodiment in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430, cable 428 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 400.

Figure 11:
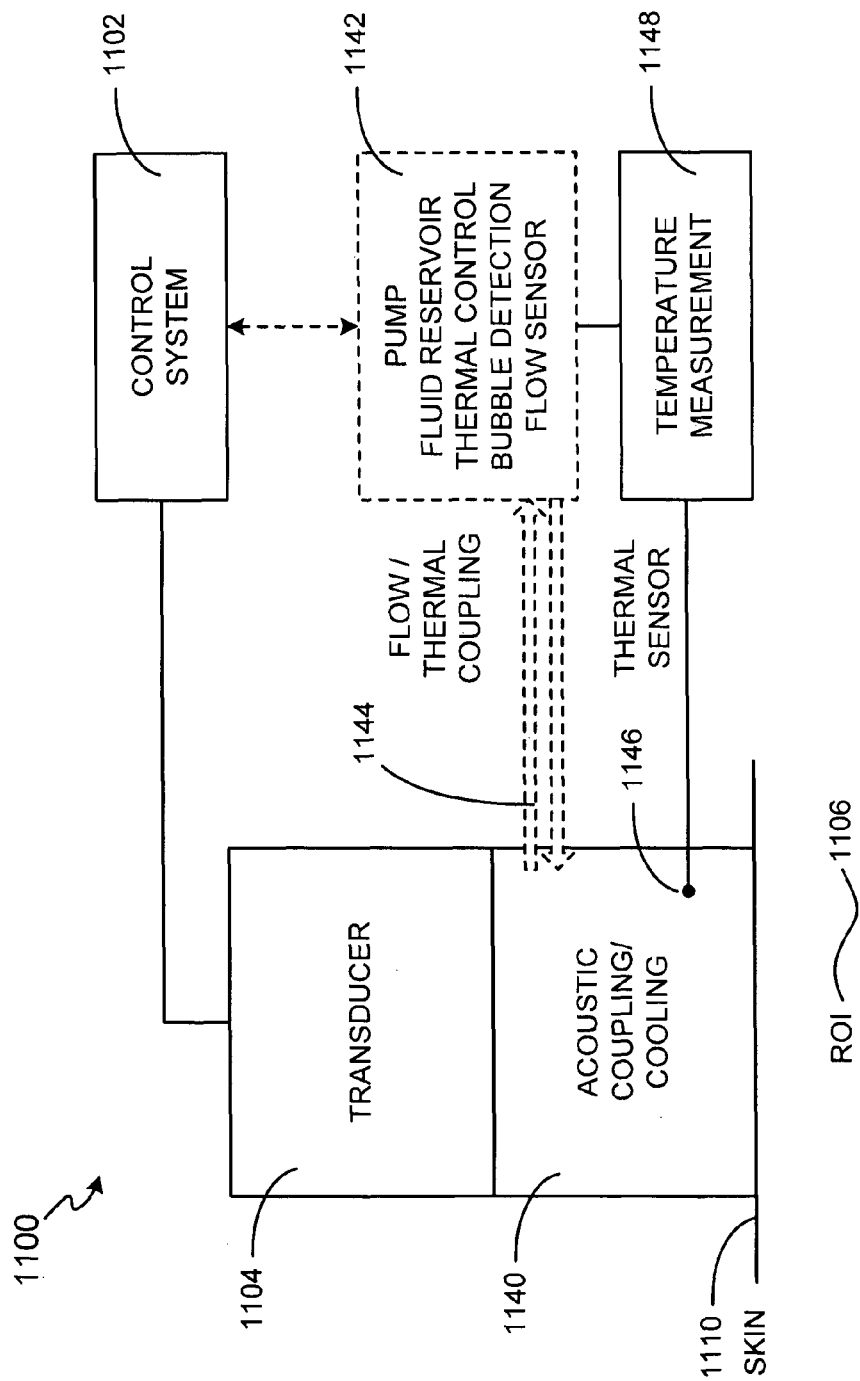
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1106, to provide thermal control at the probe 1100 to region-of-interest interface (skin) 1110 and deeper into tissue, and to remove potential waste heat from the transducer probe at region 1144. Temperature monitoring can be provided at the coupling interface via a thermal sensor 1146 to provides a mechanism of temperature measurement 1148 and control via control system 1102 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism driver 322 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of SMAS layers and targeted regions. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 400 MHz, and typically between 4 MHz and 15 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
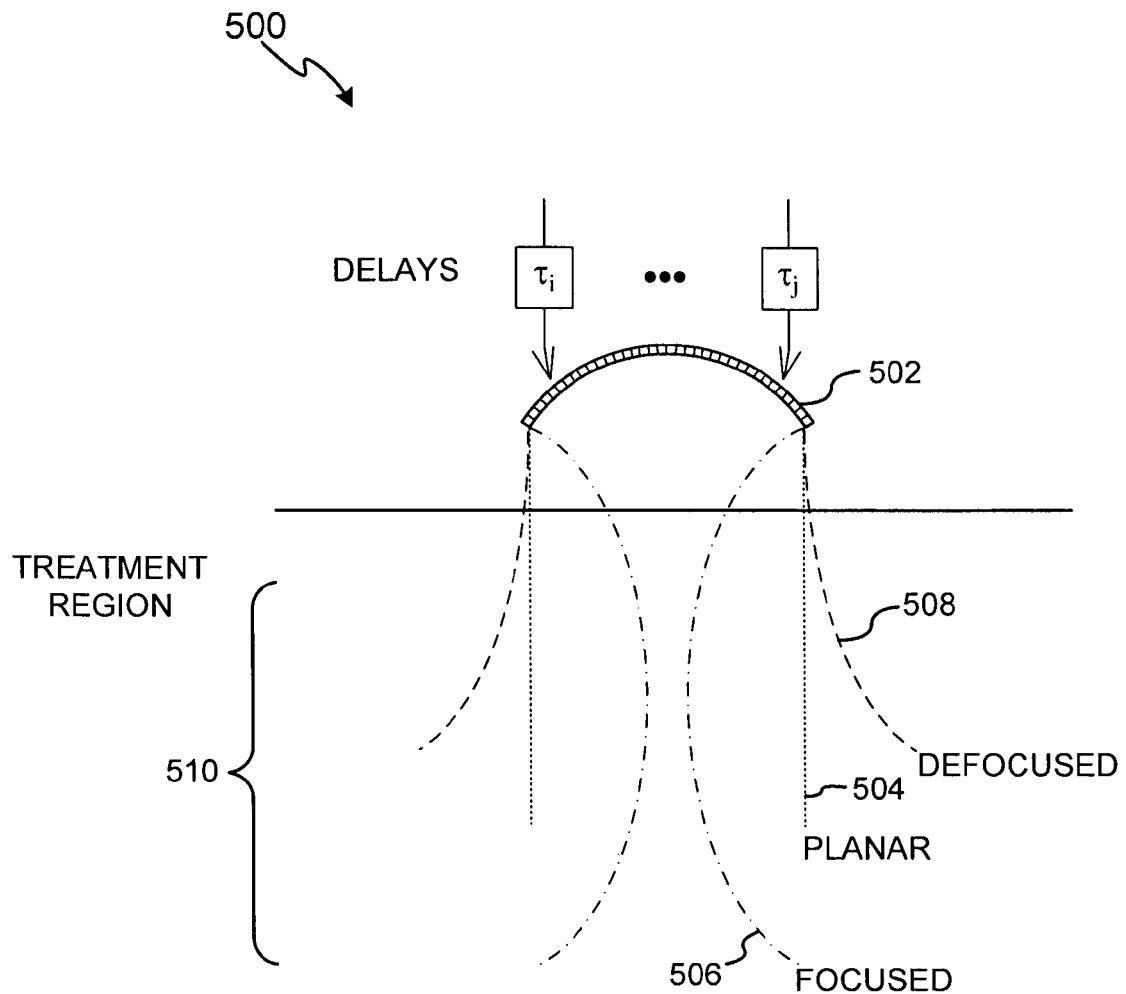
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multidirectional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 602 in combination with one or more transduction elements 606 to facilitate increased flexibility in treating ROI 610. Array 602 may be configured in a manner similar to transducer 502. That is, array 604 can be configured as an array of electronic apertures that may be operated by a variety of phases via variable electronic time delays, for example, $T_1, T_2 \ldots T_j$. By the term "operated," the electronic apertures of array 602 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
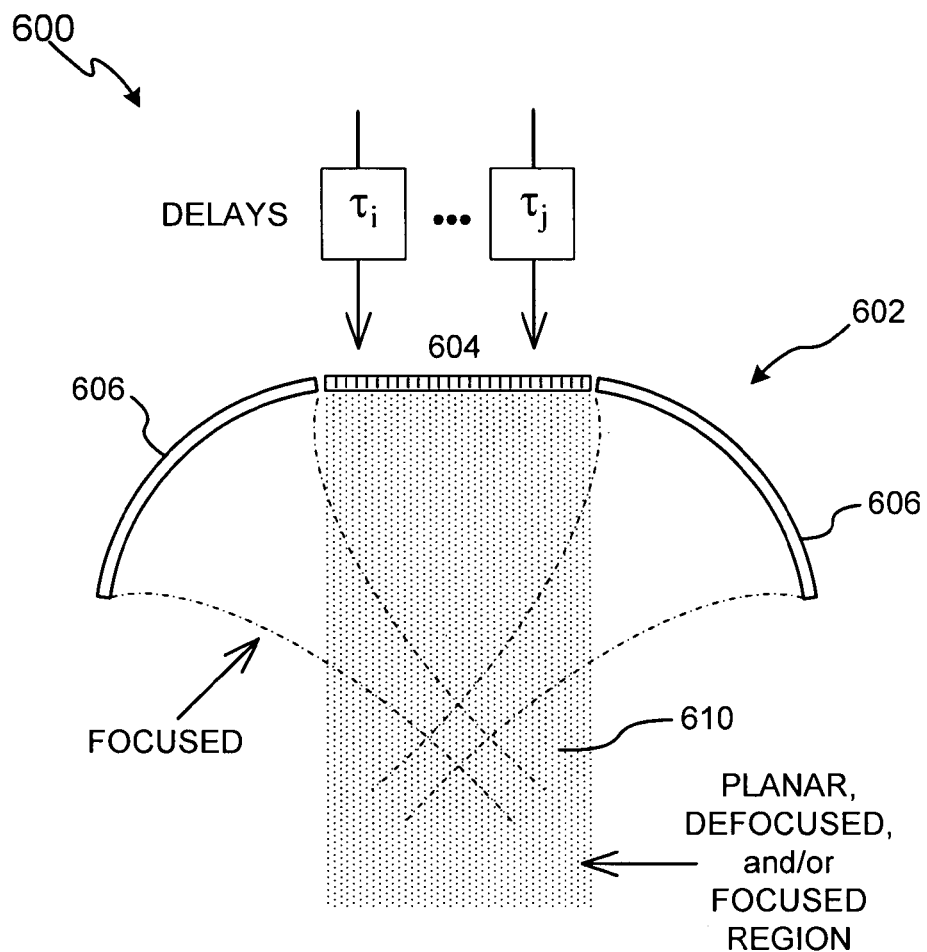
FIGS. 6A and 6B illustrate cross-sectional diagrams of an exemplary transducer in accordance with exemplary embodiments of the present invention.
Figure 6B:
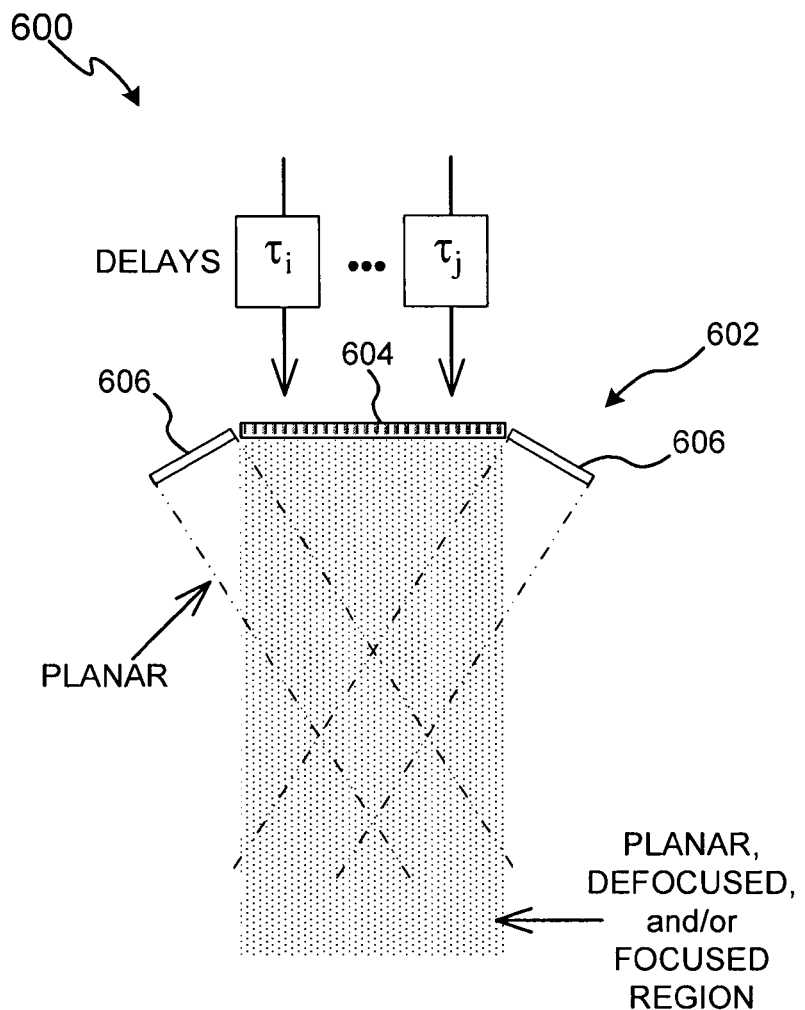

In another exemplary embodiment, depicted in FIG. 6B, transduction elements 606 can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
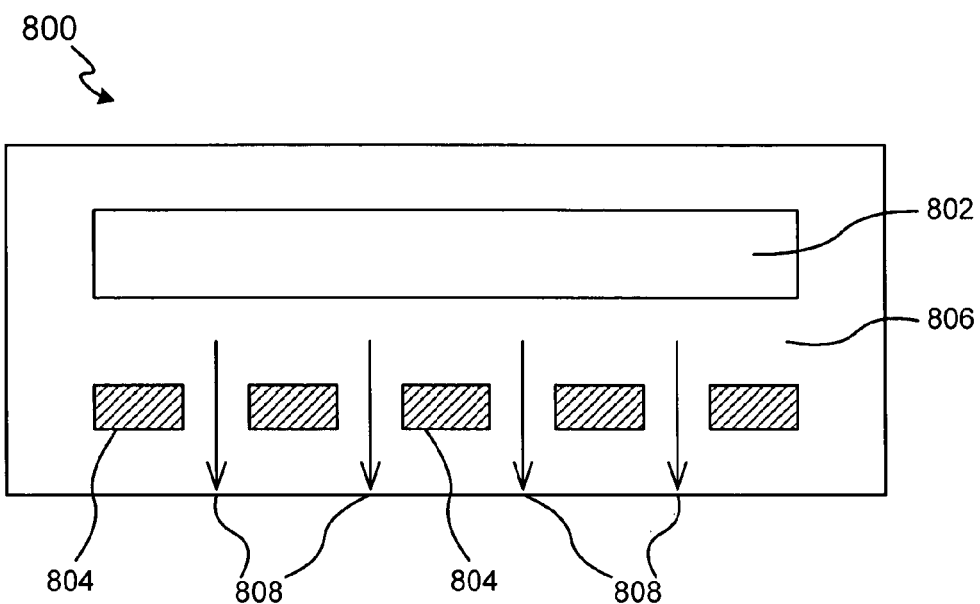
FIGS. 8A and 8B illustrate cross-sectional diagrams of an exemplary transducer in accordance with another exemplary embodiment of the present invention.
Figure 8B:
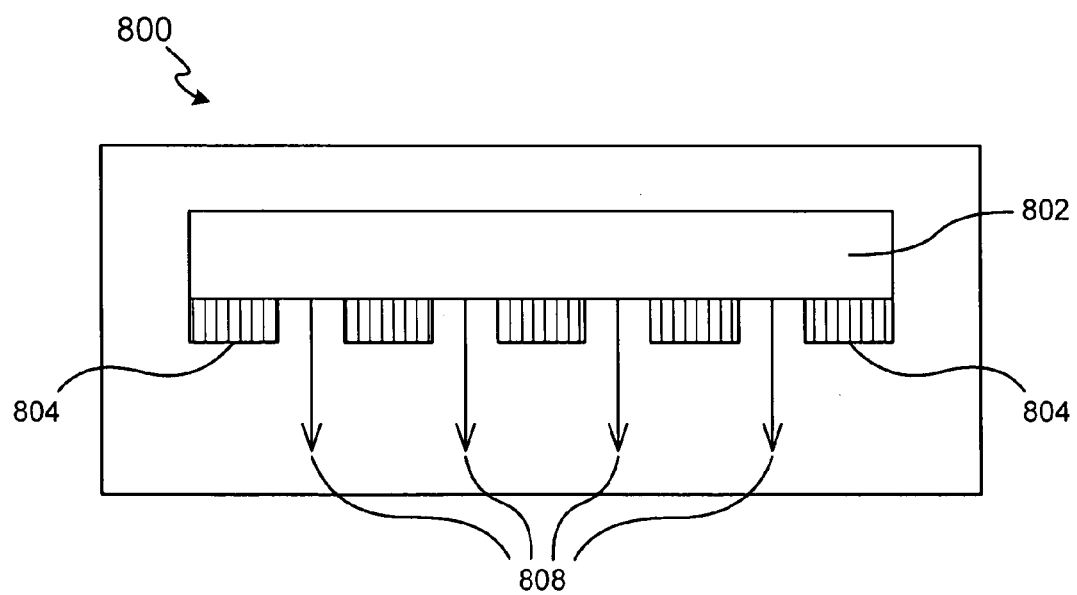

With reference to FIGS. 8A and 8B, transducer 800 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
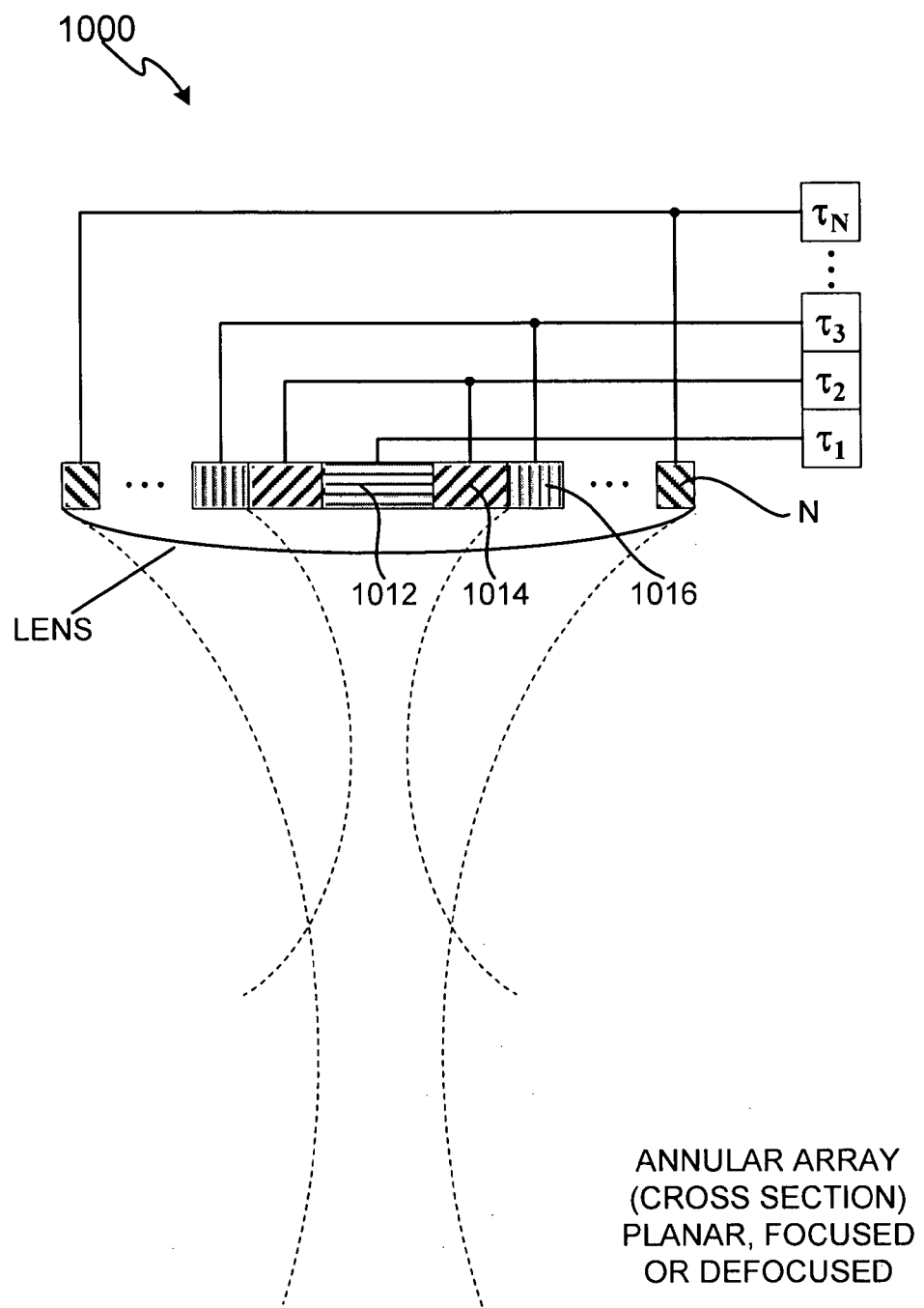
FIGS. 10A-10F illustrate cross-sectional diagrams of exemplary transducers in accordance with other exemplary embodiments of the present invention.
Figure 10B:
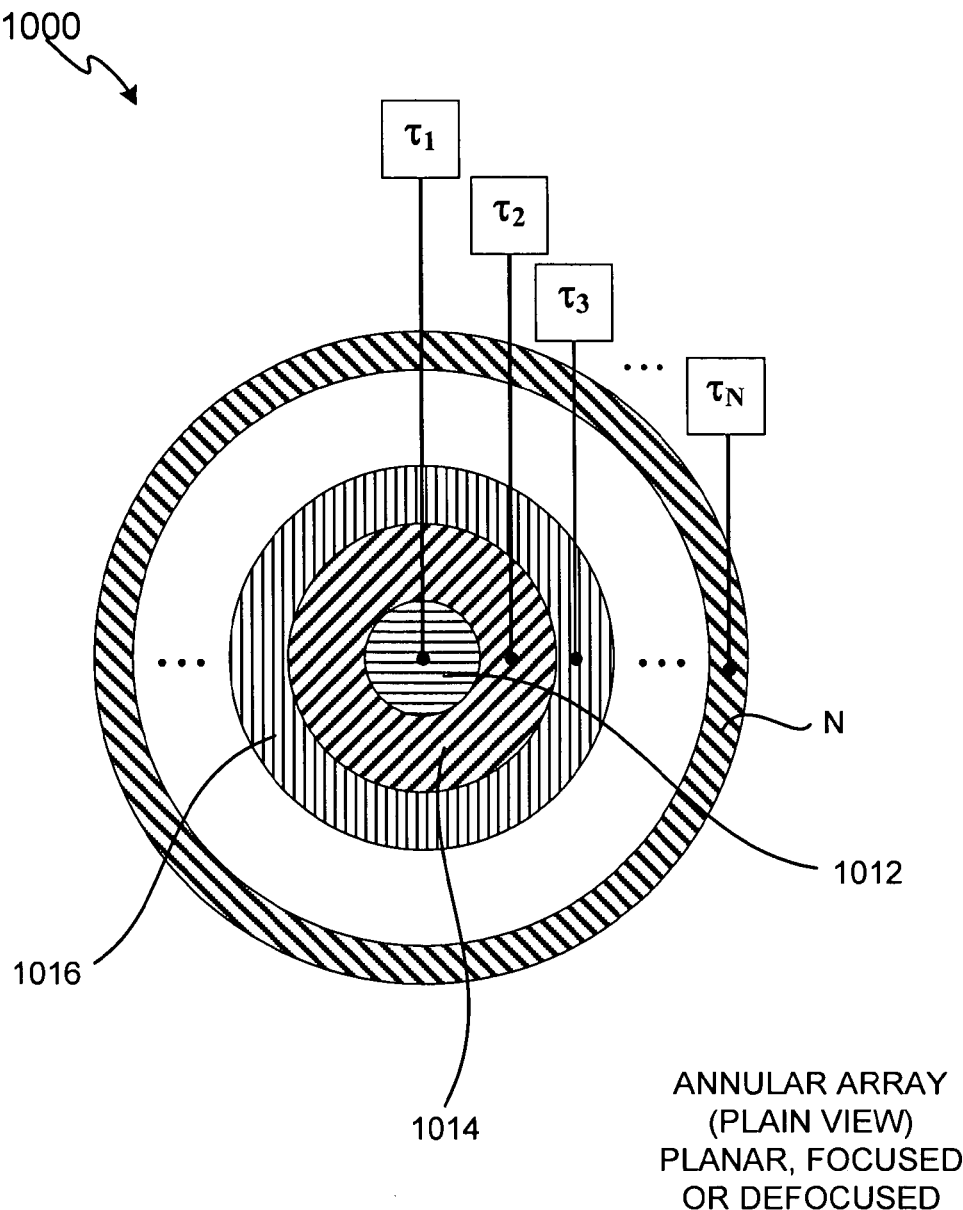
Figure 10C:
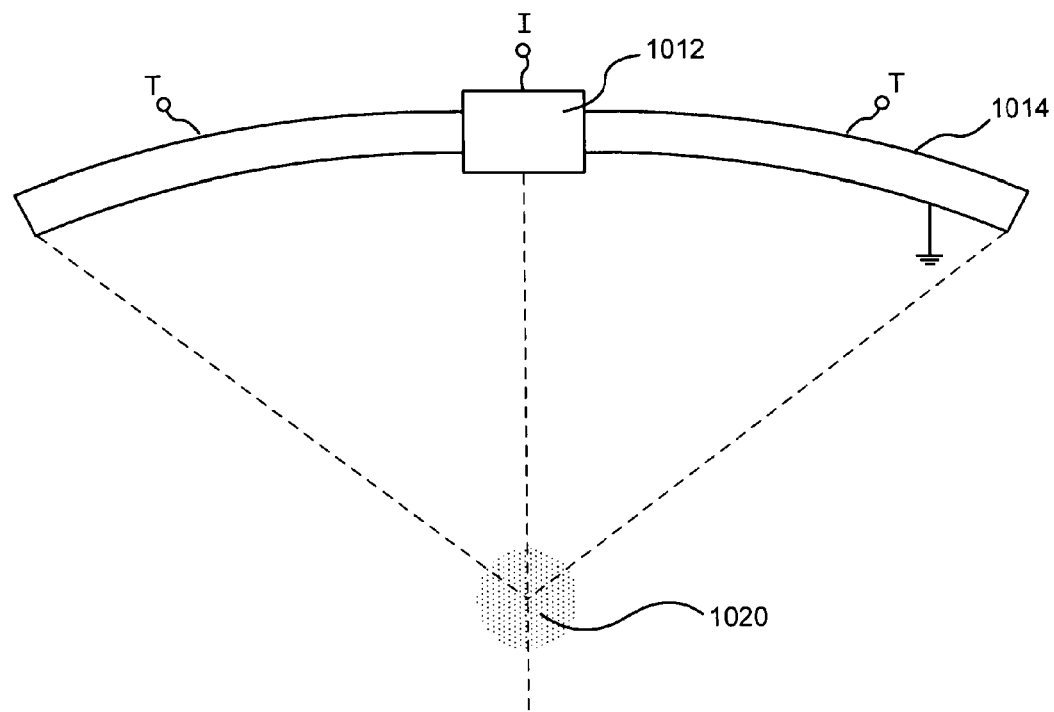
Figure 10D:
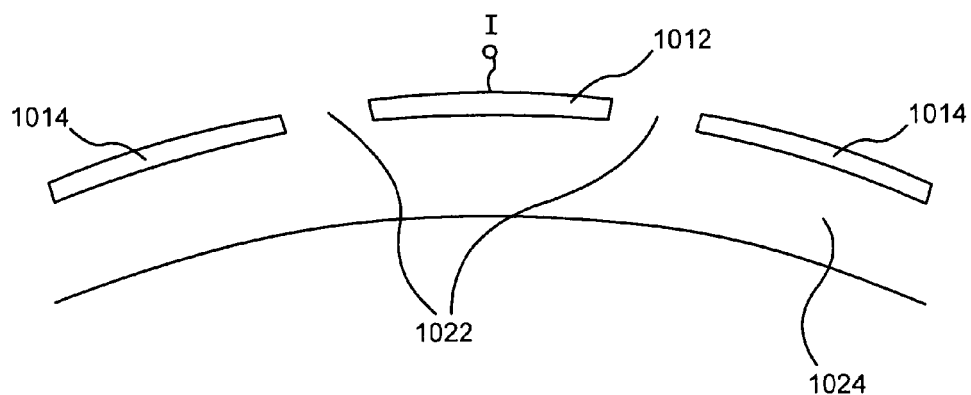
Figure 10E:
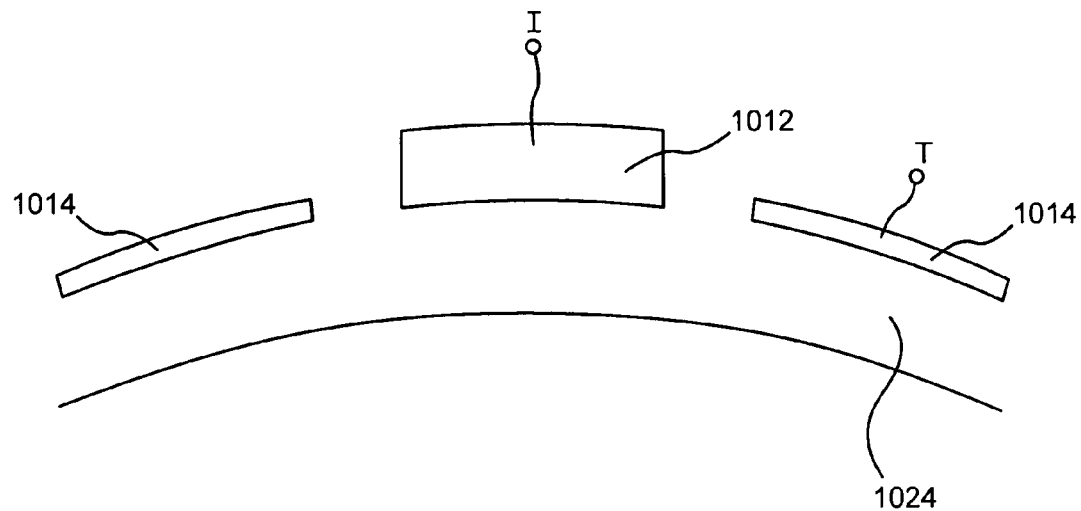

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $\tau_1, \tau_2, \tau_3 \ldots \tau_N$. An electronic focus 1020 can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 1000 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

Figure 9:
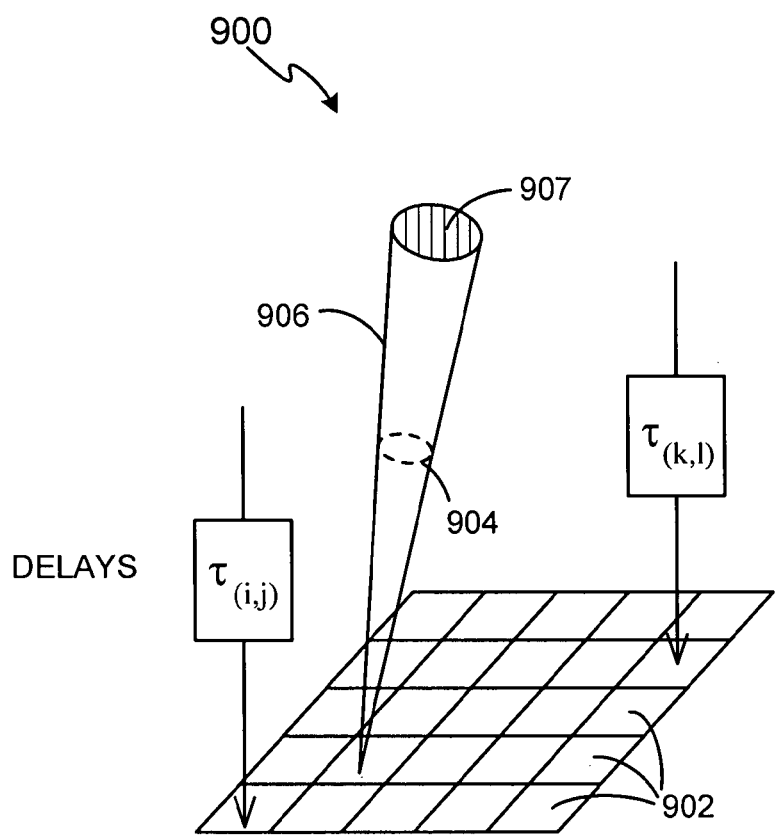
FIG. 9 illustrates an exemplary transducer configured as a two-dimensional array for ultrasound treatment in accordance with an exemplary embodiment of the present invention.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide-three dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
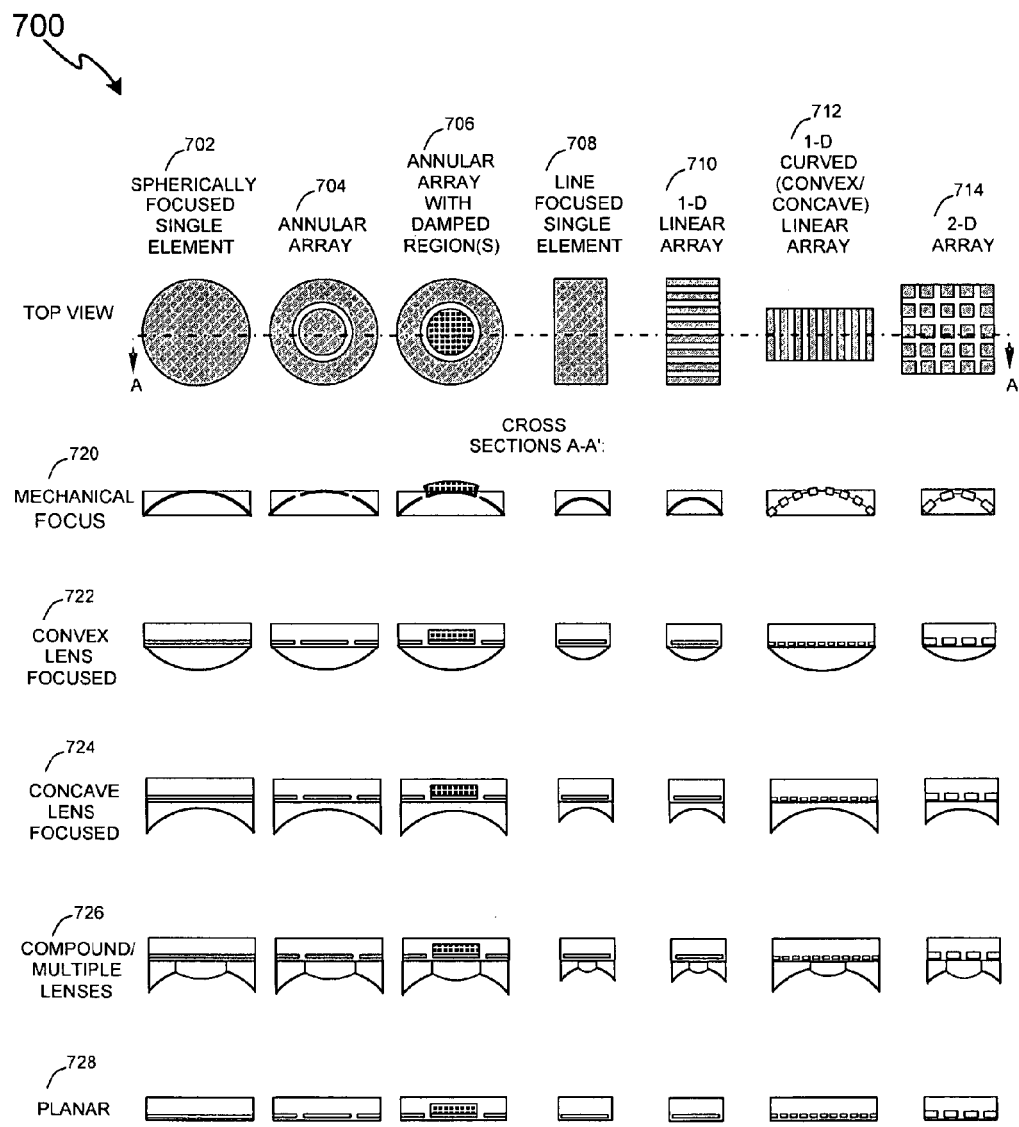
FIG. 7 illustrates exemplary transducer configurations for ultrasound treatment in accordance with various exemplary embodiments of the present invention.
Figure 10F:
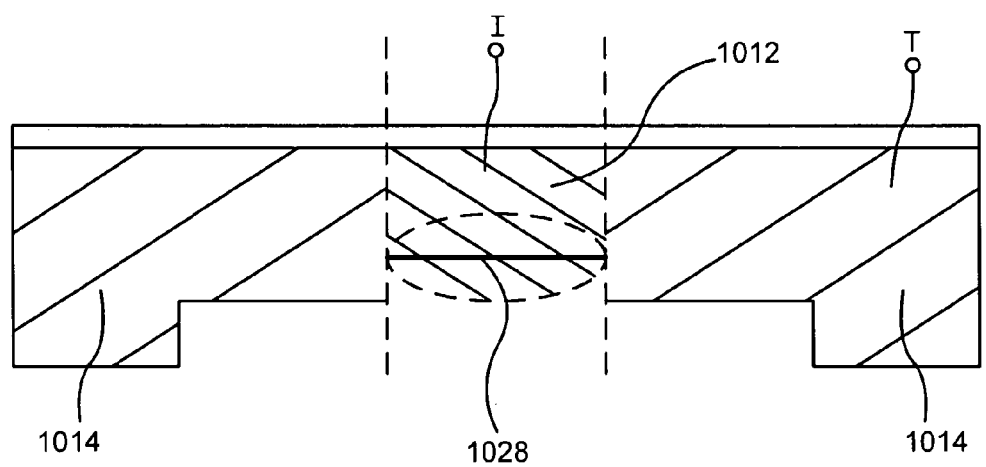

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing 712, 2-D arrays 714, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 10C-10F.

Moreover, such transduction elements 700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy.

A means of transferring energy to and from the transducer to the region of interest is provided.

Figure 12:
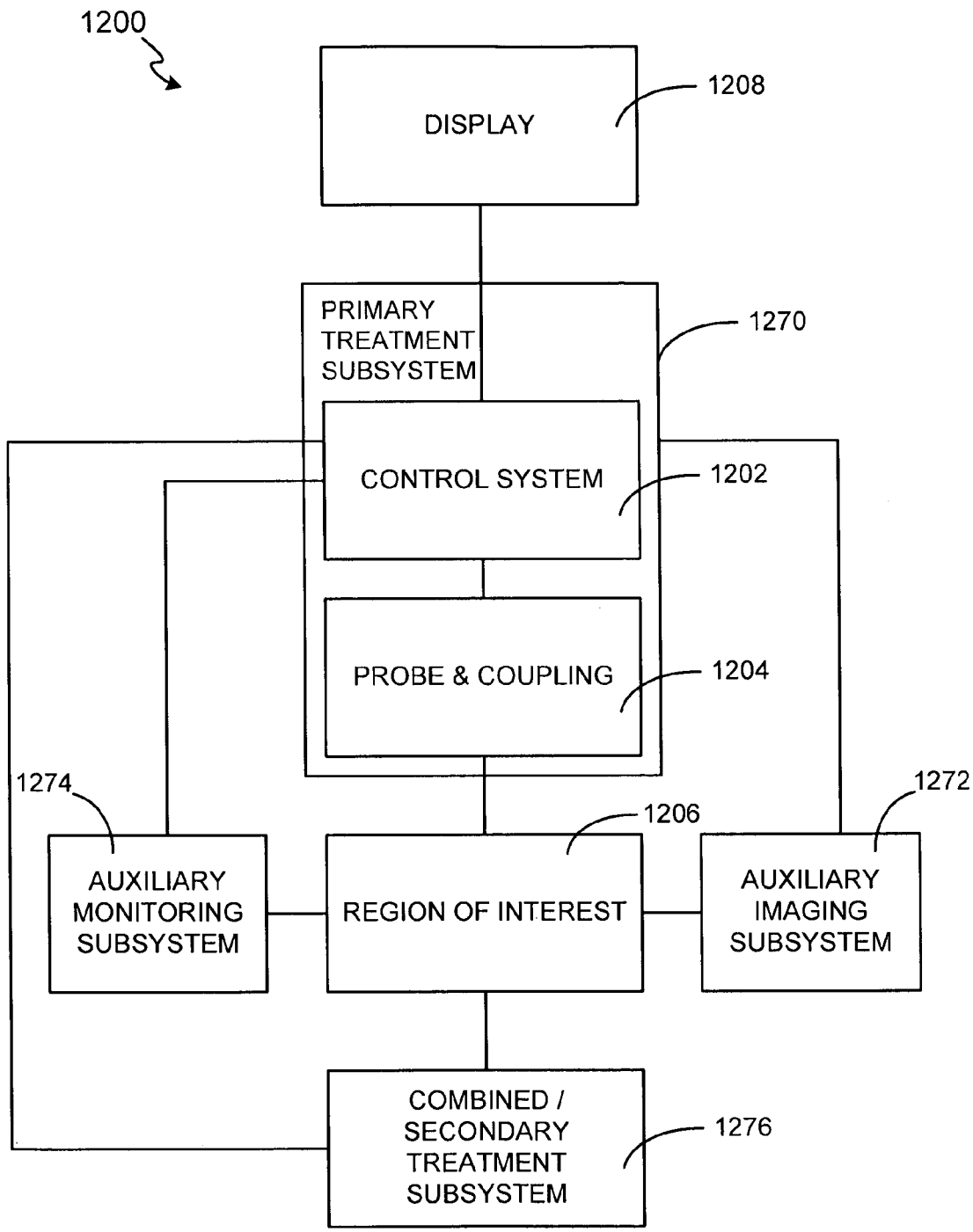
FIG. 12 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treating a region of interest 1202 can comprise a control system 1206, a probe 1204, and a display 1208. Treatment system 1200 further comprises an auxiliary imaging subsystem 1272 and/or auxiliary monitoring modality 1274 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of SMAS layers within region-of-interest 1202, including imaging/monitoring enhancements. Such imaging/monitoring enhancement for ultrasound imaging via probe 1204 and control system 1206 could comprise M-mode, persistence, filtering, color, Doppler, and harmonic imaging among others; furthermore an ultrasound treatment system 1270, as a primary source of treatment, may be combined with a secondary treatment subsystem 1276, including radio frequency (RF), intense pulsed light (IPL), laser, infrared laser, microwave, or any other suitable energy source.

Figure 13:
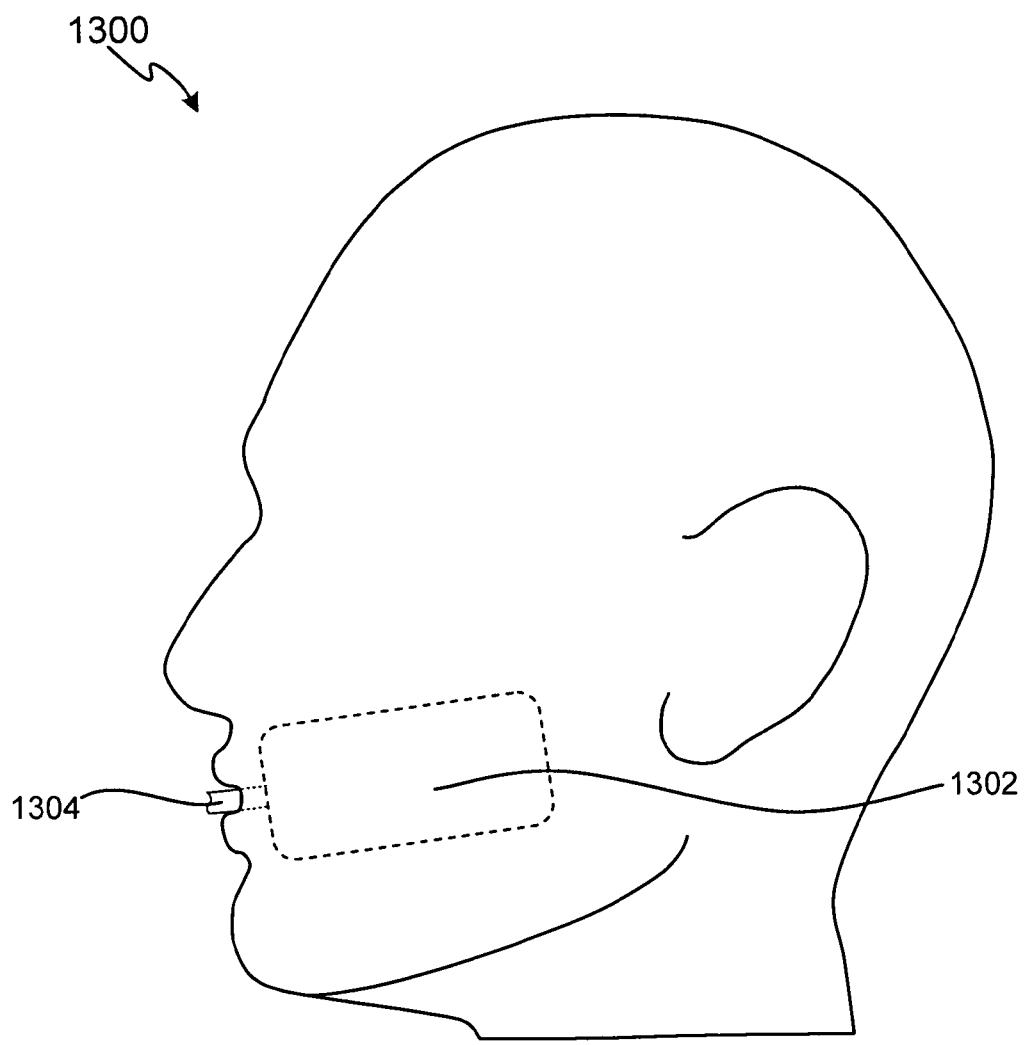
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest may be further aided, augmented, and/or delivered with passive or active devices 1304 within the oral cavity. For example, if passive or active device 1304 is a second transducer or acoustic reflector acoustically coupled to the cheek lining it is possible to obtain through transmission, tomographic, or round-trip acoustic waves which are useful for treatment monitoring, such as in measuring acoustic speed of sound and attenuation, which are temperature dependent; furthermore such a transducer could be used to treat and/or image. In addition an active, passive, or active/passive object 1304 may be used to flatten the skin, and/or may be used as an imaging grid, marker, or beacon, to aid determination of position. A passive or active device 1304 may also be used to aid cooling or temperature control. Natural air in the oral cavity may also be used as passive device 1304 whereby it may be utilized to as an acoustic reflector to aid thickness measurement and monitoring function.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

What is claimed is:

1. A method of treating the skin, the method comprising:
positioning an ultrasound probe system on a skin surface, the ultrasound probe system comprising an ultrasound therapy element and a motion mechanism;
wherein the motion mechanism is controlled by a control system in communication with the ultrasound probe;
using the ultrasound therapy element to treat a region of interest under the skin surface comprising a tissue comprising a portion of at least one of muscular fascia and SMAS tissue;
wherein the ultrasound therapy element is coupled to the motion mechanism within the probe;
wherein the ultrasound therapy element is configured for targeted delivery of ablative ultrasound energy to form a thermal lesion with at least a temperature sufficient to treat at least a portion of the tissue at a depth of up to 9 mm from the skin surface; and
activating the motion mechanism to move the ultrasound therapy element to form a plurality of the thermal lesions along a line at the depth into the tissue to cause any one of the group consisting of ablation, deactivation, and shrinkage of at least a portion of the tissue.

2. The method according to claim 1, wherein the therapy element is configured to treat with a treatment frequency of between 4 MHz and 15 MHz and wherein the plurality of thermal lesions facilitates a tightening of the tissue that leads to any one of a face lift, a treatment of laxity, and a treatment of sagging in the skin surface.

3. The method according to claim 1, wherein the depth of the lesion is within a range of 0 to 5 mm from the skin surface.

4. The method according to claim 1, wherein the depth of the lesion is within a range of 3 mm to 9 mm from the skin surface.

5. The method according to claim 1, wherein the ultrasound probe system comprises at least one combined transducer comprising an ultrasound imaging element and the ultrasound therapy element.

6. The method according to claim 1, wherein the ultrasound therapy element is a single element transducer.

7. The method according to claim 1, further comprising:
using a second ultrasound therapy element to treat the region of interest;
wherein the second ultrasound therapy element is coupled to the motion mechanism within the probe;
wherein the second ultrasound therapy element is configured for targeted delivery of ablative ultrasound energy to form a thermal lesion with at least a temperature sufficient to treat at least a portion of the tissue at a second depth of up to 9 mm from the skin surface; and
activating the motion mechanism to form a plurality of the thermal lesions along a line at the second depth into the tissue to cause any one of the group consisting of ablation, deactivation, and shrinkage of at least a portion of the tissue.

8. The method according to claim 1, wherein activating the motion mechanism within the ultrasound probe system comprises communication between and at least two of the group consisting of the control system, an accelerometer, an encoder and a position/orientation device.

9. The method according to claim 1, further comprising an imaging element configured to image with an imaging frequency of between 2 kHz to 75 MHz.

10. A method of treating the skin, comprising:
using an ultrasound device to emit ultrasound energy from a therapy element housed within an ultrasound probe to a region of interest at a depth under a skin surface in the range of 0.5 mm to 5 mm, the region of interest comprising a portion of at least one of muscular fascia and SMAS tissue, wherein emitting ultrasound energy ablates a portion of the region of interest under the skin surface to facilitate a tightening of the skin surface; and
moving a motion mechanism operably connected to the therapy element within the ultrasound probe for controllably creating a plurality of thermal lesions along a line at the depth in the range of 0.5 mm to 5 mm under the skin surface, wherein the motion mechanism comprises at least one of the group consisting of an accelerometer, encoder and a position/orientation device;

wherein the motion mechanism is controlled by a control system in communication with the ultrasound probe.

11. The method of claim 10, further comprising imaging of the region of interest with an ultrasound imaging element housed within the ultrasound probe, the imaging element configured to image with an imaging frequency of between 2 kHz to 75 MHz.

12. The method of claim 11, wherein using the ultrasound device comprises the adjustment of spatial and temporal parameters based on the imaging, wherein the imaging monitors shrinkage of the region of interest during or after emitting the ultrasound energy.

13. The method of claim 10, wherein the emitting ultrasound energy further comprises ablating adipose tissue.

14. The method according to claim 10, further comprising:
emitting ultrasound energy from a second therapy element to treat the region of interest;

wherein the second therapy element is coupled to the motion mechanism within the ultrasound probe;

wherein the second therapy element is configured for targeted delivery of ablative ultrasound energy to form a second thermal lesion with at least a temperature sufficient to treat at least a portion of the tissue at a second depth of 0.5 mm to 5 mm from the skin surface; and activating the motion mechanism to move the second therapy element within the probe to form a plurality of the second thermal lesions along a line at the second depth into the tissue to cause any one of the group consisting of ablation, deactivation, and shrinkage of at least a portion of the tissue.

15. A method for treating the skin, comprising:
focusing therapeutic ultrasound energy from a therapy element to a treatment region comprising a portion of at least one of SMAS tissue and muscular fascia at a depth in the range of up to 9 mm below the skin surface, wherein the therapeutic ultrasound energy ablates a portion of the treatment region to facilitate tissue tightening at the treatment region, wherein the therapy element is housed within an ultrasound probe; and moving a motion mechanism operably connected to the therapy element within the ultrasound probe for controllably creating a plurality of thermal lesions along a line at the depth at the treatment region, wherein the motion mechanism is controlled by a control system in communication with the ultrasound probe, wherein the control system controls at least one of a spatial parameter and a temporal parameter.

16. The method of claim 15, further comprising imaging of the region of interest with an ultrasound imaging element housed within the ultrasound probe, the imaging element configured to image with an imaging frequency of between 2 kHz to 75 MHz.

17. The method of claim 15, wherein the focusing therapeutic ultrasound energy further comprises ablating adipose tissue.

18. The method of claim 16, further comprising displaying at least one thermal lesion at the depth on a display electrically connected to the ultrasound imaging element.

19. The method of claim 15, wherein the therapy element is a single element transducer.

20. The method according to claim 15, further comprising:
focusing therapeutic ultrasound energy from a second therapy element to treat the treatment region;

wherein the second therapy element is coupled to the motion mechanism within the ultrasound probe;

wherein the second therapy element is configured for targeted delivery of ablative ultrasound energy to form a second thermal lesion with at least a temperature sufficient to treat a second portion of the treatment region at a second depth of up to 9 mm below the skin surface; and moving the motion mechanism to move the second therapy element within the ultrasound probe to form a plurality of the second thermal lesions along a second line at the second depth into the tissue to cause any one of the group consisting of ablation, deactivation, and shrinkage of at least a portion of the treatment region.

* * * * *